United States Patent [19]

Neckers et al.

[11] Patent Number: 5,623,080
[45] Date of Patent: Apr. 22, 1997

[54] FLUORONE AND PYRONIN Y DERIVATIVES

[75] Inventors: Douglas C. Neckers, Perrysburg, Ohio; Jianmin Shi, Webster, N.Y.

[73] Assignee: Spectra Group Limited, Inc., Maumee, Ohio

[21] Appl. No.: 388,802

[22] Filed: Feb. 15, 1995

Related U.S. Application Data

[60] Division of Ser. No. 154,880, Nov. 19, 1993, Pat. No. 5,451,343, which is a continuation-in-part of Ser. No. 881,048, May 11, 1992, abandoned, and Ser. No. 772,103, Oct. 7, 1991, abandoned, which is a continuation-in-part of Ser. No. 756,611, Sep. 9, 1991, abandoned, which is a continuation-in-part of Ser. No. 702,886, May 20, 1991, abandoned.

[51] Int. Cl.$^6$ .................. C07D 311/82; C07D 311/78; C07D 495/12; A01N 43/02
[52] U.S. Cl. .................. 549/393; 546/58; 546/61; 546/79; 546/110; 546/24; 546/25; 546/26; 546/27; 546/28; 546/223; 546/224; 546/225; 546/385; 546/391; 546/392; 546/394
[58] Field of Search .................. 252/582, 589; 549/24, 25, 26, 27, 28, 223, 224, 225, 385, 391, 392, 393, 394; 546/58, 61, 79, 110; 514/455

[56] References Cited

U.S. PATENT DOCUMENTS

| | | | |
|---|---|---|---|
| 1,885,592 | 11/1932 | Coulthard et al. | |
| 2,875,047 | 2/1959 | Oster | 96/35 |
| 4,481,136 | 11/1984 | Khanna et al. | |
| 4,492,762 | 1/1985 | Wang et al. | 436/537 |
| 4,552,830 | 11/1985 | Reardon et al. | 430/281 |
| 4,585,862 | 4/1986 | Wang et al. | 544/319 |
| 4,716,097 | 12/1987 | Weed | 430/327 |
| 4,772,530 | 9/1988 | Gottschalk et al. | 430/138 |
| 4,852,017 | 7/1989 | Hunkapiller | 364/497 |
| 4,855,225 | 8/1989 | Fung et al. | 435/6 |
| 4,883,750 | 11/1989 | Whiteley et al. | 435/6 |
| 5,093,245 | 3/1992 | Keith et al. | 435/91 |
| 5,096,530 | 3/1992 | Cohen | 156/229 |
| 5,137,800 | 8/1992 | Neckers et al. | 430/281 |

FOREIGN PATENT DOCUMENTS

| | | | |
|---|---|---|---|
| 90/10254 | 9/1990 | European Pat. Off. | G03F 7/031 |
| 0507493 | 3/1992 | European Pat. Off. | C08G 77/385 |
| 0530095 | 8/1992 | European Pat. Off. | C08F 2/50 |
| 59-176641 | 6/1984 | Japan | G01M 3/20 |
| 1058516 | 2/1967 | United Kingdom | A61K 3/00 |
| 1123767 | 8/1968 | United Kingdom | D06P 3/76 |

OTHER PUBLICATIONS

Janijie et al., "Multigand Interactions . . . ," *JACS* 111:6374–6377 (1989).
Phillips and Read, "Novel Radical Couplings . . . ," *J. Chem. Soc.*, 671–73 (1986).
Shapovalov, "Study of spectral and acid–base properties . . . ," *Chem. Abs.* 101:564761, 1984.
Shen, "A study on 6–hydroxyfluorone . . . ," *Chem. Abs.* 107:156351d, 1987.
Wang et al., "Study on a new chromogenic reagent . . . ," *Chem. Abs.* 115:246974d, 1991.
Amt–Guerri et al., "Synthesis and Spectroscopic Properties . . . ," *Chem. Abs.* 112:236887b, 1990.
Amt–Guerri et al., "Singlet Oxygen Photogeneration . . . ," *Photochem. and Photobio.* 53:199–210 (1990).
Flossman et al., "Mechanism of the color reaction of DNA . . . ," *Chem. Abs.* 76:46433r, 1972.
Hobbs et al., "Preparation of (aminoalkynyl) nucleotides . . . ," *Chem. Abs.* 109:93540h, 1988.

*Primary Examiner*—Shean C. Wu
*Attorney, Agent, or Firm*—Thompson Hine & Flory LLP

[57] ABSTRACT

A compound of the formula (I) or (II):

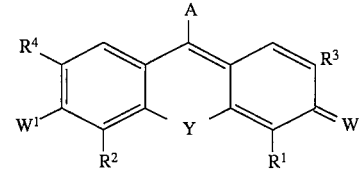

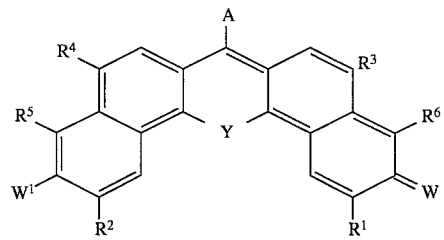

where $R^1$, $R^2$, $R^5$ and $R^6$ are the same or different and represent a hydrogen atom or a halogen atom and $R^1$ and $R^2$ may combine to form a ring; $R^3$, and $R^4$ are the same or different and represent a hydrogen atom, a halogen atom, a benzoyl group, a group of the formula —L(CH$_2$)$_n$R$^8$ where n is 1 to 8, $R^8$ is a hydrogen, hydroxy, amino, dialkylamino, —COR$^{16}$ or —COOR$^{14}$ where $R^{16}$ is a hydrogen, chlorine, COCl, C$_1$–C$_8$ alkyl, —NR$_2$ or aryl and $R^{14}$ is a hydrogen, C$_1$–C$_8$ alkyl, aryl, COR, 2,4-dinitrophenyl, N-imido or —NR$_2$ and L is a direct bond or C=O; W is =O; W$^1$ is hydrogen or —OR$^9$, where $R^9$ is hydrogen, C$_1$–C$_8$ alkyl, acyl or a group of the formula —(CH$_2$)$_n$R$^{10}$ where n is 1 to 8 and $R^{10}$ is amino, dialkylamino, hydroxy, acryloyl or methacryloyl; Y is oxygen, sulfur, selenium, tellurium, C=O, or >N—R$^{13}$ is where $R^{13}$ is 4-methylphenyl, and A is hydrogen, alkenyl, dichlorotriazinylamino, or an electron withdrawing group selected from the group consisting of COOR$^{11}$, C(O)OCOR$^{11}$, CONR$_2$, CN, NO$_2$, NCS, NCO, SO$_2$R$^{12}$, SO$_3$, R$^{12}$, SO$_3$R$^{11}$, SO$_2$NR$_2$ and CX$_3{}^2$ where X$^2$ is the same or different and is a halogen atom and $R^{11}$ is hydrogen, alkyl, aryl, or aralkyl, and $R^{12}$ is hydrogen, alkyl, aryl, or aralkyl; provided that when $R^1$–$R^6$ are all hydrogen, A is not hydrogen.

20 Claims, No Drawings

FLUORONE AND PYRONIN Y DERIVATIVES

This application is a divisional of application Ser. No. 08/154,880, filed Nov. 19, 1993, U.S. Pat. No. 5,451,343, which is a combined continuation-in-part of U.S. application Ser. No. 07/881,048, filed May 11, 1992, now abandoned, and No. 07/772,103, filed Oct. 7, 1991, now abandoned, which in turn is a continuation-in-part of Ser. No. 07/756,611, filed Sep. 9, 1991, now abandoned, which in turn is a continuation-in-part of Ser. No. 07/702,886, filed May 20, 1991, now abandoned.

The present invention relates to a novel class of compounds which absorb light at wavelengths greater than 350 nm and are useful as fluorescers or as photoinitiators. The present invention provides compounds of the formulas (I) and (II) and their equivalents (the nomenclature of the compounds used herein is based on the numbering of positions as shown in formula (I)):

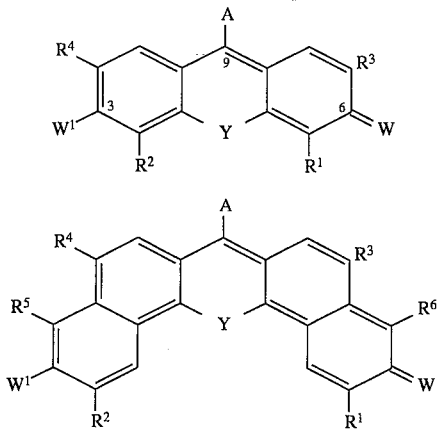

where $R^1$, $R^2$, $R^5$ and $R^6$ are the same or different and represent a hydrogen atom or a halogen atom and $R^1$ and $R^2$ may combine to form a ring; $R^3$ and $R^4$ are the same or different and represent a hydrogen atom, a halogen atom, a benzoyl group, a group of the formula —L(CH$_2$)$_n$R$^8$ where n is 1 to 8, $R^8$ is hydrogen, hydroxy, amino, dialkylamino, —COR$^{16}$, or —COOR$^{14}$ where $R^{16}$ is hydrogen, chlorine, COCl, C1–C8 alkyl, NR$_2$, aryl, and $R^{14}$ is hydrogen, C1–C8 alkyl, aryl, COR, 2,4-dinitrophenyl, N-imido or NR$_2$ and L is a direct bond or >C=O; W is =O or =NR$^+_2$Z$^-$ where R is hydrogen or lower alkyl and Z$^-$ is a counter ion, when W is =O, $W^1$ is hydrogen or —OR$^9$ where $R^9$ is hydrogen, C1–C8 alkyl, acyl or a group of the formula —(CH$_2$)$_n$R$^{10}$ where n is 1 to 8 and $R^{10}$ is amino, dialkylamino, hydroxy, acryloyl or methacryloyl and when W is =NR$^+_2$Z$^-$, $W^1$ is hydrogen or —NR$_2$; Y is oxygen, sulfur, selenium, tellurium, >C=O, or N—R$^{13}$ where $R^{13}$ is 4-methylphenyl, A is hydrogen, alkenyl, alkyl, or an electron withdrawing group (EWG); provided that when $R^1$–$R^6$ are all hydrogen, A is not hydrogen or methyl.

A further embodiment of the invention is ionically bonded complexes of the aforesaid compounds in which W is O and $W^1$ is —OR$^9$ and one or two iodonium cations. When $W^1$ is O$^-$ as in TIHF below, the compounds are believed to form ionic complexes with iodonium cations at the 3- and 6-positions in a ratio of 2 cations per complex. When $W^1$ is not O$^-$ as in an alkoxy group as in DIBF below, the compounds are believed to form ionic complexes with an iodonium cation at the 6-position in a ratio of 1 cation per complex.

Depending upon structure and substitution, the compounds of the invention absorb visible light or infrared radiation and fluoresce or act as electron donors or electron acceptors in photoinitation. As contrasted with conventional fluorescein dyes, the addition of a strong EWG at the 9 position corresponding to A extends the wavelength of maximum absorption approximately 100 nm to longer wavelengths.

In accordance with some of preferred embodiments of the invention, the compounds of the invention more particularly include fluorone and pyronin Y derivatives of the formula the (III) and (IV):

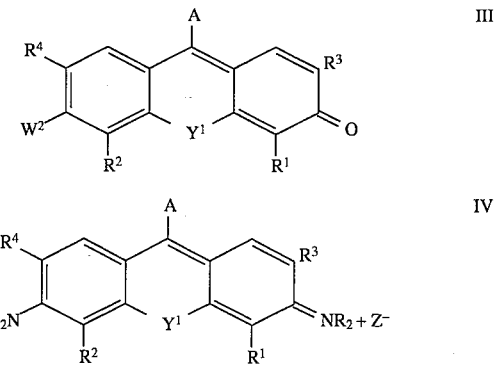

where A is selected from the group consisting of hydrogen, alkyl, alkenyl, alkynyl, dichlorotriazinylamino, and electron withdrawing groups (EWG) which are stronger electron withdrawing groups than a phenyl group or a halogen-substituted or a carboxyl-substituted phenyl group; $Y^1$ is oxygen, sulfur or >NR$^{13}$ where $R^{13}$ is 4-methylphenyl; R, and $R^1$–$R^4$ are defined as above; Z is a counter ion and $W^2$ is hydrogen or —OR$^9$ and $R^9$ is defined as above.

The compounds of the invention can be more specifically represented by the formula (V):

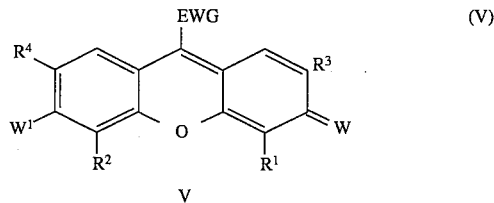

where $R^1$–$R^4$ may be the same or different and are defined as above; EWG is an electron withdrawing group selected from the group consisting of COOR$^{11}$, COR$^{12}$, C(O)O-COR$^{11}$, CONR$_2$, CN, NO$_2$, NCS, NCO, SO$_2$R$^{12}$, SO$_3$R$^{11}$, SO$_2$NR$_2$, CX$_3^2$; $R^{11}$ is hydrogen, alkyl, aryl, or aralkyl; $R^{12}$ is hydrogen, alkyl, aryl, or aralkyl, $X^2$ can be the same or different and is a halogen atom; and W and W' are selected from the group consisting respectively of =O and O— and =NR$_2$+ and —NR$_2$ where R is defined as above. When the compounds are fluorescers one of A, $R^3$ and $R^4$ may be a linking group (for example R, $R^{11}$ or $R^{12}$ as defined above may be, N-imido such as N-succinimido and N-maleimido, or NR$_2$). When $R^{11}$ is N-imido or —NR$_2$ the compounds are esters of N-hydroxyimides such as N-hydroxysuccinimides or N-hydroxyamines.

In the photoinitiators of the invention at least one and preferably at least two of $R^1$–$R^6$ is a halogen atom and more particularly an iodine or bromine atom. A is hydrogen or cyano in a particularly preferred class of photoinitiators. For use in photoinitiation $W^1$ is preferably butoxy or octyloxy. When $R^{10}$ is an acrylolyl or methacryloyl group, a polymerizable initiator is provided.

In the fluroescers of the invention $R^1$–$R^6$ cannot be bromine or iodine and $R^9$ must be hydrogen when $W^1$ is —OR$^9$. To exhibit fluorescence, the compounds must be ionized. In one embodiment of the invention, $R^4$ may be a moiety which produces intramolecular ionization of the compound at W/W$^1$. For intramolecular ionization at least one of $R^3$–$R^4$ will have a basic functional group when W/W$^1$ is O/O$^-$ and have an acid functional group when W/W$^1$ is $NR_2^+$/$NR_2$. Examples of such moieties are acetyl and amino groups.

In one embodiment of the invention the compounds may be linked to an antibody or a ligand analog for use in immunoassays. For use in immunoassays, at least one of A, $R^3$ or $R^4$ includes a functional group (hereafter a "coupling group") such as an amino group, a carboxyl group, a tert-butoxycarbonyl group (TBOC), a sulfinyl group, a sulfonyl group, an isocyanato group, an isothiocyanato group, a halogen atom, an N-hydroxysuccinimide ester or a N-hydroxy maleimide ester, etc. which enables the compound to be coupled with a ligand analog, an antibody or similar substrate.

In another embodiment the compounds may be substituted with one or more oleophilic moieties which make the compounds soluble in oil and useful as fluorescent dyes for oil leak detection or as oil soluble photoinitiators. The oil solubility of the compounds can be tailored to a particular application by the addition of longer chain, e.g., C4–C8 groups at one or more of $R^3$, $R^4$ and $W^1$. For example, the compounds may be substituted at $R^3$, $R^4$ and $W^1$ by alkyl, alkylcarbonyl, carboxyalkyl or alkylcarboxyalkyl groups. For use as a fluorescent dye in oil leak detection $R^3$ and/or $R^4$ may be substituted by t-butyl or longer chain substituted or unsubstituted alkyl. The addition of alkyl groups at the 2 and 7 positions extends absorption in the red at least an additional 20 nm, increases the fluorescence quantum yield, and decreases the bleaching rate.

The invention also provides tracers useful in immunoassays of the formula (VI):

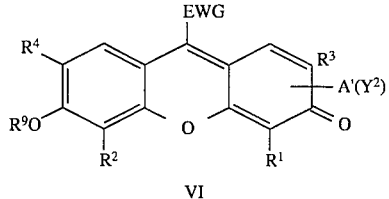

VI where $Y^2$ is a linking group and A' is a ligand-analog as defined in U.S. Pat. No. 4,585,862 or an antibody, and EWG is defined as above. U.S. Pat. No. 4,585,862 is incorporated herein by reference. In one embodiment, the linking group $Y^2$ is the divalent analog of one of the aforesaid functional groups defined for EWG, $R^3$ or $R^4$. Particularly useful linking groups include an oxalyl group, a sulfonyl group, a sulfinyl group, a hydroxyimido ester group, a group of the formula —$(CH_2)_n$—$R^{15}$ where $R^{15}$ is oxalyl chloride, carbonyl chloride (COCl), nitrobenzoate ester (e.g., a 2,4-dinitrophenyloxycarbonyl), N-hydroxyimido groups, TBOC esters, or a carboamidosulfonyl or a carboamidosulfinyl group. In another embodiment the antibody or ligand-analog may be linked to the tricyclic nucleus via the moiety $X^3$ in formula (VII) below. In still another embodiment linkage may be via the A moiety at the 9-position. One compound which may be useful in immunoassays is substituted by hydrogen at the 9-position and cyano, isocyanato or isothiocyanato at one of the 2, 4, 5 and 7 positions.

Representative examples of alkyl groups referenced with respect to the compounds of formula (I)–(VI) above are straight chain, branched chain and cyclic alkyl groups having 1 to 10 carbon atoms.

Representative examples of aryl groups include phenyl groups which may be unsubstituted or substituted by alkyl, $(CH_2)_p$ $COOR^{11}$, $(CH_2)_p X^2$, $(CH_2)_p X^2$, $(CH_2)_p NR_2$, where R, $R^{11}$ and $X^2$ are defined as above and p is 0 to 6.

Representative examples of aralkyl groups include aralkyl groups containing 7 to 20 carbon atoms such as benzyl, phenethyl, etc.

Representative examples of alkaryl groups include alkaryl groups containing 7 to 20 carbon atoms such as phenyl substituted at the ortho or para position by a straight chain or branched chain alkyl group having 1 to 6 carbon atoms.

Representative examples of alkenyl groups include alkenyl groups having 2 to 10 carbon atoms such as vinyl, allyl, 1-propenyl, 1-butenyl and 1,3-butadienyl.

Representative examples of alkynyl groups include alkynyl groups having up to 10 carbon atoms such as 1-propynyl, 1-butynyl, etc.

Representative examples of acyl groups are groups of the formula —OCR where R is alkyl or p-aryl such as methyl or phenyl.

Representative examples of the halogen atoms include fluorine, chlorine, bromine and iodine and, more particularly, fluorine or chlorine in the case of fluorescers and bromine or iodine in the case of photoinitiators.

Representative examples of electron withdrawing groups include $COOR^{11}$, $COR^{12}$, $C(O)OCOR^{11}$, $CON_2$, CN, $NO_2$, NCS, NCO, $SO_2R^{12}$, $SO_3R^{11}$, $SO_2NR_2$, $CX_3^2$ where $X^2$, $R^{11}$ and $R^{12}$ are defined above.

The term "N-imido" as used herein refers to groups such as N-maleimido and N-succinimido.

When $R^1$ and $R^2$ combine to form a ring, the compounds in accordance with the invention can be represented by the formula VII.

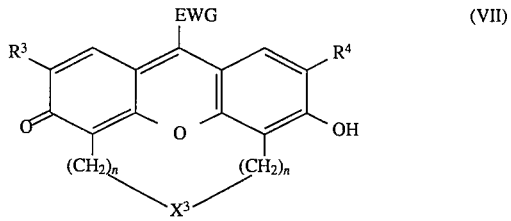

where EWG, $R^3$ and $R^4$ are defined as above, n is 2 or 3, and $X^3$ is >NH, >$NR^{13}$, O, S, $PR^{17}$, $CHR^{17}$ where $R^{17}$ has the same definition as $R_3$–$R^4$ but can be the same as or different than $R_3$–$R^4$ and may additionally represent dichlorotriazinyl.

Representative examples of the counter ion represented by Z include chloride, bromide, iodide, perchlorate when Z is an anion and monovalent ions such as K$^+$, Na$^+$, ammonium, phosphonium, etc. when Z is a cation. When W/W' is O/O$^-$, Z may be hydrogen.

Representative examples of photoinitiators in accordance with the invention include:

1. 5,7-diiodo-3-methoxy-6-fluorone (DIMF)
2. 5,7-diiodo-3-ethoxy-6-fluorone (DIEF)
3. 5,7-diiodo-3-butoxy-6-fluorone (DIBF)
4. 5,7-diiodo-3-octoxy-6-fluorone (DIOF)
4a. 4,5-diiodo-3-hydroxy-6-fluorone
5. 9-cyano-5,7-diiodo-3-methoxy-6-fluorone (CDIMF)
6. 9-cyano-5,7-diiodo-3-ethoxy-6-fluorone (CDIEF)
7. 9-cyano-5,7-diiodo-3-butoxy-6-fluoorone (CDIBF)
8. 9-cyano-5,7-diiodo-3-octoxy-6-fluorone (CDIOF)
9. 3-hydroxy-2,4,5,7-tetraiodo-6-fluorone (TIHF)
10. 3-hydroxy-2,4,5,7-tetrabromo-6-fluorone (TBHF)
11. 3-hydroxy-2,4,5,7-tetrachloro-6-fluorone (TCHF)
12. 3-hydroxy-2,4,5,7-tetrafluoro-6-fluorone (TFHF)

13. 9-cyano-3-hydroxy-2,4,5,7-tetraiodo-6-fluorone (TIHCF)
14. 9-cyano-3-hydroxy-2,4,5,7-tetrabromo-6-fluorone (TBHCF)
15. 9-cyano-3-hydroxy-2,4,5,7-tetrachloro-6-fluorone (TCHCF)
16. 9-cyano-3-hydroxy-2,4,5,7-tetrafluoro-6-fluorone (TFHCF)
17. 3-hydroxy-4,5,7-triiodo-2octanoyl-6-fluorone
18. 9-cyano-3-hydroxy-4,5,7-triiodo-2-octanoyl-6-fluorone
19. 3-hydroxy-4,5,7-triiodo-2-octanoyl-6-fluorone
20. 9-cyano-3-hydroxy-4,5,7-triiodo-2-octyl-6-fluorone
21. 3-hydroxy-2,4,5,7-tetraiodo-6-thiafluorone
22. 3-hydroxy-4,5,7-triiodo-2-pentanoyl-6-fluorone
23. 9-cyano-3-hydroxy-4,5,7-triiodo-2-pentanoyl-6-fluorone
24. 3-hydroxy-4,5,7-triiodo-2-pentyl-6-fluorone
25. 9-cyano-3-hydroxy-4,5,7-triiodo-2-pentyl-6-fluorone
26. 2,7-di-t-butyl-4,5-diiodo-3-hydroxy-6-fluorone
27. 9-cyano-2,7-di-t-butyl-4,5-diiodo-3-hydroxy-6-fluorone
28. 7-benzoyl-2,4,5-triiodo-3-hydroxy-6-fluorone Representative examples of fluorescers in accordance with the invention include:

29. 3-hydroxy-6-thiafluorone
30. 2,7-di-t-butyl-3-hydroxy-6-fluorone
31. 9-cyano-2,7-di-t-butyl-3-hydroxy-6-fluorone
32. 2,7-di-t-butyl-4,5-carboxymethyl-3-hydroxy-6-fluorone
33. 9-cyano-2,7-di-t-butyl-4,5-carboxymethyl-3-hydroxy-6-fluorone
34. 9-trifluoromethyl-2,7-di-t-butyl-3-hydroxy-6-fluorone
35. 9-trifluoromethyl-2,7-di-t-butyl-4,5-carboxymethyl-3-hydroxy-6-fluorone
36. 9-trifluoromethyl-3-hydroxy-6-fluorone
37. 3-hydroxy-7-pentanoic acid-6-fluorone
37a. 3-hydroxy-7-butyric acid-6-fluorone
37b. 9-cyano-3-hydroxy-7-butyric acid-6-fluorone
38. 9-cyano-1-hydroxy-7-pentanoic acid-6-fluorone
39. 2,7-dicitronellic acid-3-hydroxy-6-fluorone
40. 9-cyano-2,7-dicitronellicacid-3-hydroxy-6-fluorone
41. 9-cyanopyronin-Y
42. 2,7-di-t-butylpyronon-Y
43. 9-cyano-2,7-di-t-butylpyronin-Y
44. Compound I.

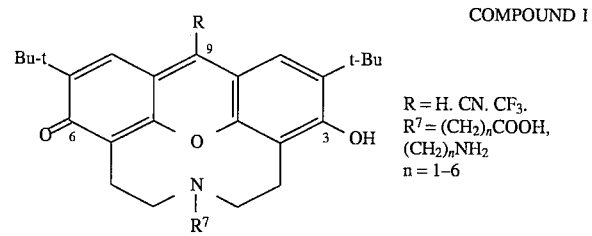

COMPOUND I

R = H. CN. CF$_3$.
R$^7$ = (CH$_2$)$_n$COOH, (CH$_2$)$_n$NH$_2$
n = 1–6

Compounds 37, 37a, 37b, 39 and 40 are 7-carboxy derivatives which can be converted to the N-hydroxysuccinimide ester, the N-maleimide, the t-BOC ester or the acid chloride is introduce linking groups therein.

In accordance with the invention, compounds are provided which absorb at wavelengths greater than 450 nm and preferably greater than 550 nm. In most compounds, these longer wavelengths of maximum absorption are believed to be attributable to the presence of a strong EWG at the 9-position. Preferred among these are moieties which extend resonance conjugation such as cyano. This effect is illustrated in the following table for compounds of the formula (I) wherein the substituents are as defined as in the following Table 1:

TABLE 1

| Y$^1$ | W/W' | A | R$^1$ | R$^2$ | R$^3$ | R$^4$ | λmax in EtOH | ε |
|---|---|---|---|---|---|---|---|---|
| O | O/O$^-$ | H | H | H | H | H | 504 | 24700 |
| O | O/O$^-$ | CN | H | H | H | H | 594, 548 | 50300, 24700 |
| O | O/O$^-$ | H | Br | Br | Br | Br | 530 | 39300 |
| O | O/O$^-$ | CN | Br | Br | Br | Br | 626, 576 | 51400, 24500 |
| O | O/O$^-$ | H | I | I | I | I | 536 | 91200 |
| O | O/O$^-$ | CN | I | I | I | I | 638, 586 | 80000, 35000 |
| O | O/O$^-$ | H | I | I | I | I | 520 | 86000 |
| O | O/O$^-$ | CN | I | I | I | I | 618, 570 | 30500, 16600 |
| O | O/O$^-$ | H | H | H | t-But | t-Bu | 518 | 101000 |
| O | O/O$^-$ | CN | H | H | t-But | t-Bu | 614, 564 | 47400, 23200 |
| O | O/O$^-$ | H | I | I | t-But | t-Bu | 532 | 90800 |
| O | O/O$^-$ | CN | I | I | t-But | t-Bu | 636, 582 | 68300, 33600 |
| 0 | O/OMe | H | I | I | I | H | 470 | 23,500 |
| O | O/OEt | H | I | H | I | H | 470 | 21,100 |
| O | O/OBu | H | I | H | I | H | 470 | 30,200 |
| O | O/OOc | H | I | H | I | H | 470 | 31,600 |
| O | O/OBu | CN | 1 | H | I | H | 600 (down) broad | — |
| O | O/O$^-$ | H | H | H | H | (CH$_2$)$_3$COOEt | 510 | — |
| O | O/O$^-$ | H | H | H | H | (CH$_2$)$_3$COOK | — | — |
| O | O/O$^-$ | H | H | H | H | (CH$_2$)$_3$COOH | — | — |
| O | O/O$^-$ | CN | H | H | H | (CH$_2$)$_3$COOH | 596 | 74,000 |
| O | O/O$^-$ | H | H | H | H | (CH$_2$)$_4$COOH | — | — |
| O | O/O$^-$ | CN | H | H | H | (CH$_2$)$_4$COOH | — | — |
| O | O/O$^-$ | H | H | H | H | (CH$_2$)$_3$COOH | 512 | — |
| O | O/O$^-$ | H | I | H | I | CO(CH$_2$)$_6$CH$_3$ | 538 | 84,800 |
| O | O/O$^-$ | CN | I | H | I | CO(CH$_2$)$_6$CH$_3$ | 636 | 17,000 |
| O | O/O$^-$ | H | I | H | I | (CH$_2$)$_7$CH$_3$ | 534 | 92,600 |
| O | O/O$^-$ | CN | I | H | I | (CH$_2$)$_7$CH$_3$ | 630 | 40,000 |

TABLE 1-continued

| Y¹ | W/W' | A | R¹ | R² | R³ | R⁴ | λmax in EtOH | ε |
|---|---|---|---|---|---|---|---|---|
| O | O/O (CH₂)₆ OCOCH=CH₂ | H | I | H | I | H | 472 | |
| 0 | O/O- | H | | H | H | H | (CH₂)₃COONHS ester* | |
| 0 | O/O- | CN | | H | H | H | (CH₂)₃COONHS ester | |
| NφCH₃ | NH₂/NH₂+ | H | H | H | H | H | 472 | |
| NφCH₃ | NH₂/NH₂+ | H | I | I | I | I | 472 | |
| S | O/O⁻ | H | H | H | H | H | 524 | |
| S | O/O⁻ | CN | H | H | H | H | 610 | |
| S | O/O⁻ | H | I | I | I | I | — | |

*NHS = N-hydroxysuccinimide

As the table indicates, in accordance with certain embodiments, the compounds absorb strongly in the range of 650–700 nm.

Certain more specific embodiments of the invention are fluorescers of the formula (IV) where R is methyl and more particularly, R is methyl and A is hydrogen or cyano; photoinitiators of the formula (III) where A is hydrogen or cyano and two or more of $R^1$–$R^4$ are iodo or bromo and preferably iodo and still more preferably compounds of the formula (III) in which $R^1$ and $R^3$ are iodo, or $R^1$ and $R^2$ are iodo, or $R^1$, $R^2$ and $R^3$ are iodo, or $R^1$, $R_2$, $R^3$ and $R^4$ are iodo; fluorescers of the formula (III) where $R^1$, $R^2$ and $R^3$ are hydrogen, A is hydrogen or cyano, and $R^4$ is substituted to enhance solubility or with a linking group.

The synthesis of fluorones in accordance with the present invention is illustrated in Scheme 1 below and by the following Synthesis Examples.

SYNTHESIS EXAMPLE 1

3,6-Dihydroxyxanthone 2,2',4,4'-Tetrahydroxybenzophenone (2.5 g, 10.15 mmol.) was heated in 20 ml of water at 195°–200° C. for 4 hours (Aldrich pressure tube). After cooling, the crude product was filtered off and mixed with 25 ml of water. The resulting suspension was refluxed for 25 min. and filtered at about 60° C. Pure product 3,6-dihydroxyxanthone 2.15 g was obtained in 90.4% yield. It did not melt below 330° C. HNMR (DMSO): 10.780 (s,2H), 7.983 (d,2H,J=8.6 Hz), 6,822 (m,4H). MS: 228,220, 1717, 115, 100, 69, 63.

SYNTHESIS EXAMPLE 2

3,6-Dihydroxyxanthane

To a suspension of 3,6-dihydroxyxanthone (46 g, 201 mmol.) obtained as in Example 1 in 1.6 L of THF was added over 1 hr 800 ml of borane-tetrahydrofuran complex (1.0M in THF, caution very vigorous raction at beginning). This mixture was stirred overnight under argon at room temperature to give a clear yellow solution. The excess diborane was decomposed by careful addition of water followed by 1N HCl to give a clear yellow solution. The tetrahydrofuran was removed by rotary evaporation and the resulting solid filtered, washed with water and redissolved in 10% NaOH. This solution was filtered, cooled and reprecipitated with slow addition of HCl to give a yellow solid which was filtered, washed with water and dried under vacuum to give 40.14 g (93%, mp 207–208) of 3,6-Dihydroxyxanthane. H¹NMR (DMSO): 9.41 (s, 2H); 6.97 (d, 2H, J=8.4 Hz), 6.4 (dd, 2H, J=8.4, 2.4 Hz), 6.39 (d, 2H, J=2.4 Hz), 3.765 (s, 2H).

SYNTHESIS EXAMPLE 3

2,4,5,7-Tetraiodo-3-hydroxy-6-fluorone (TIHF)

Iodic acid (16.4 g, 93 mmol) dissolved in a minimum amount of water (app. 1 ml per gram) was added dropwise over 20 min. to a solution of 10 g (46.7 mmol) of 3,6-dihydroxyxanthane and 29.8 g (118 mmol) of iodine in 1 L of absolute ethanol. This mixture was stirred over two hours during which the dark brown solution slowly turned a red orange as the solid initiator precipitated. The mixture was then warmed for an hour at 60° C. After cooling, the mixture was filtered, washed with water and ethanol and the crude solid tritiated with absolute ethanol and refiltered to give, after drying under vacuum, 29 g (87%) of a red solid (λ=536 nm in ethanol) H¹NMR (DMSO) 8.31 (s, 2H), 8.07 (S, 1H).

SYNTHESIS EXAMPLE 4

3-Hydroxy-6-fluorone

To a solution of 3,6-dihydroxyxanthane (2.14 g 10 mmol) obtained as in example 2 in 60 ml of ethanol at 25° C. was added DDQ (2.78 g, 12 mmol). The reaction mixture was stirred for 8 hours at room temperature. The yellow precipitate was filtered off and washed with ethanol. 3-Hydroxy-6-fluorone (1.9 g) was obtained in 90% yield. NMR (DMSO): 8.203 (s, 1H), 7,589 (d, 2H, J=8.6 Hz), 6.659 (d, 2H, J=9.2 Hz), 6.478 (s, 2H). λmax=500 nm (MeOH).

SYNTHESIS EXAMPLE 5

2,4,5,7-Tetrabromo-3-hydroxy-6-fluorone (TBHF)

To a solution of 3,6-dihydroxyxanthane (4.28 g 20 mmol) in 150 ml of ethanol was added sodium hydroxide solution (4.8 g, 120 mmol in 10 ml of H₂O). The solution was cooled to 0° C. then Br₂ (22.4 g, 140 mmol) was slowly added. After addition, the reaction mixture was stirred for 8 hrs. at room temperature. Precipitate was filtered off and washed with ethanol 2,4,5,7-tetrabromo-3-hydroxy-6-fluorone (9.16 g 90.8%) was obtained. NMR (DMSO) 8.309 (s, 1H), 8.244 (s, 2H), λmax=526 nm (methanol).

In Table 2 below, the properties of the foregoing initiators are shown:

TABLE 2

| Compound | λmax$^a$ | λf$^b$ | φf | pKa | Eox | Ered | φphos |
|---|---|---|---|---|---|---|---|
| HF | 500,504,490 | 506,513 | .95$^c$ | 5.97 | 1.34 | −.99 | — |
| TBHF | 526,530,516 | 539 | .52 | 3.28 | 1.099 | −.95 | — |
| TIHF | 532,536,526 | 544,549 | .13 | 4.08 | 1.04 | −.95 | 676 |

Entries in the table are in the solvents according to the following order.

a. MeOH, EtOH, 10% MeOH/90% water

SYNTHESIS EXAMPLE 6

2,4,5,7-Tetraiodo-9-cyano-3-hydroxy-6-fluorone

Potassium cyanide (1.175 g, 18.0 mmol) was added to a solution of TIHF (10.74 g 15.0 mmol) in 100 ml of DMF. The reaction was monitored by its visible spectrum until all of the TIHF was consumed. The solvent was removed with a vacuum pump at room temperature and the residue was treated with 1:1 hexane/dichloromethane. The precipitate was filtered, dried and treated with 18% HCl then washed with water. 2,4,5,7-tetraiodo-9-cyano-3-hydroxy-6-fluorone (10.60 g) was obtained (975). HNMR (DMSO): 8.006 (2H,s) max (EtOH=638 nm).

SYNTHESIS EXAMPLE 7

6-hydroxy-3-methoxyxanthone 7.0 g (30.7 mmol) of 3,6-dihydroxyxanthone is dissolved in aq. NAOH (2.5 g(62.5 mmol) in 200 mls $H_2O$). 3.2 mls (33.6 mmol) of dimethylsulfate is added dropwise with stirring, and solid forms immediately upon completion. Stirred further 1 hour and heated to reflux for 15 minutes. Additional base is added to insure complete solubility of phenols. The solution is acidified with HCl, and filtration yields a mixture of staring material and the target compound. Solid is heated to reflux in about 200 mls ethanol for 15 minutes to dissolve starting material, and solid is filtered out, washing with ethanol and water. This may have to be repeated several times to obtain pure compound in about 50% yield; mp=303-306-C.NMR (200 $MH_z$ in d-DMSO) s 3.89 (3H,s), 6.82 (1H,d,J=2.24 $H_z$), 6.87 (1H,m), 6.99 (1H, dd,J=8.78 $H_z$, 2.20 $H_z$),, 7.09 (1H,d,J=2.26 $H_z$), 7.99 (1H, d,J=8.52 $H_z$), 8.03 (1H,d,J=8.78 $H_z$).

SYNTHESIS EXAMPLE 8

6-hydroxy-3-methoxyxanthone

To a solution of 4.0 g (16.5 mmol) of 6-hydroxy-3-methooxyxanthone in 150 mls of anhydrous THF under nitrogen is added with stirring 41 mls (41 mmol) of 1M $BH_3$ in THF. Reaction mixture is stirred overnight at room temperature. Solvent is stripped and flask washed out with aq. NaOH, dissolving product completely. After filtration to remove impurities, the solution is acidified, filtered and washed with water to yield 3.73 g (99%) of yellow product xanthane. NMR (200 $MH_z$ in d-DMSO) s 3.72 (3H,s), 3.82 (2H,s), 6.46 (2H,M), 6.63 (2H,m), 7.00 (1H,d,J=8.12 $H_z$), 7.10 (1H,d,J=9.46 $H_z$). MS: 227,212,197,184,128.

The synthesis of 5,7-diiodo-3-alkoxy-6-fluorones and their 9-cyano derivatives is shown in the following Synthesis Examples 9-17.

SYNTHESIS EXAMPLE 9

5,7-Diiodo-3-methoxy-6-fluorone

To a solution of 0.228 g (1 mmol) of 6-hydroxy-3-methoxyxanthane and 0.508 g (4 mmol) of iodine in 20 mls of ethanol, 0.211 g (1.2 mmol) of iodic acid in minimum water is added dropwise with stirring. Precipitate forms immediately, and reaction is stirred 1 hour at room temperature when warmed to 50-C for 15 minutes. Filtration and washing with ethanol and water yields 0.44 g (92%) of orange 5,7-diiodo-3-methoxy-6-fluorone. NMR (200 $MH_z$ in d-DMSO) s 3.96 (3H,s), 7.10 (1H,dd,J=8.72 $H_z$,2.38 $H_z$), 7.19 (1H,d,J-2.38), 7.86 (1H,d,J=8.74 $H_z$), 8.35 (1H,s), 8.46 (1H,s). MS: 478,450,351,323,196,181,125.

SYNTHESIS EXAMPLE 10

3-Butoxy-6-hydroxyxanthone 3,6-Dihydroxy xanthone (1,60.7 mmol) was dissolved into hot basic water ($Na_2CO_3$ 240 mmol in 600 ml water). After the 3,6-dihydroxy xanthone was completely dissolved, the temperature was controlled to 70° C. Isopropyl alcohol (10 ml) was added to the reaction mixture and butyl bromide (180 mmol) was added dropwise. The reaction mixture was stirred rigorously for 72 hours. A white precipitate appeared which was then filtered and washed with water. There was almost no disubstituted compound in the product. This precipitate was dissolved in 3% NaOH, filtered and finally reprecipitated with HCl yielding 90% of 3-butoxy-6-hydroxy xanthone.

Continuous efforts have been made to improve the reaction conditions for a synthesis of 3-butoxy-6-hydroxy xanthone. The results of attempts to increase the yield by changing various reaction conditions in Example 10 are shown in Table 3.

TABLE 3

|  | Run-1 | Run-2 | Run-3 | Run-4 | Ref. |
| --- | --- | --- | --- | --- | --- |
| Concentration of Xanthone (wt %) | 6.9 | 5 | 5 | 5 | 2.3 |
| Water/i-PrOH (volume) | 60/1 | 9/1 | 60/1 | 30/1 | 60/1 |
| Temperature (°C.) | 70 | 80 | 70 | 70 | 70 |
| Reaction time (hours) | 72 | 72 | 100 | 72 | 72 |
| Monobutyl xanthone (%) | 38 | 23 | 73 | 81 | 90 |
| Dibutyl xanthone (%) | trace | 65 | trace | trace | trace |
| Starting material (%) | 60 | 11 | 11 | 22 | 10 |

The increase of i-ProH ratio and the temperature (Run-2) drastically boosted the yield of side product, dibutyl xanthone. Run-3 showed that a slight reduction of the concentration could improve the yield of monobutyl xanthone, but it is still not a satisfying yield even with a prolonged reaction time. An increase of i-ProH (Run-4) could improve the yield of monobutyl xanthone keeping the side product only at a trace amount.

SYNTHESIS EXAMPLE 11

3-Octoxy-6-hydroxy xanthone 3,6-Dihydroxy xanthone (1,20 mmol) was dissolved in hot mixture of basic water (80 mmol of $Na_2CO_3$ in 100 ml of water) and 50 ml of methanol. After the compound was completely dissolved, a methanol solution of octyl bromide (40 mmol in 50 ml of methanol) was added dropwise and the reaction mixture was stirred rigorously for 120 hours at refluxing temperature. The reaction mixture was cooled to room temperature giving a precipitate. This white precipitate was then filtered, washed with water, and washed with hot hexane to remove the disubstituted side product. 3-Octoxy-6-hydroxy xanthone was obtained in 30% yield. $^1$HNMR (DMSO): d11.0(1H,s), 8.05 (1H,d,J=6.0 Hz), 8.02 (1H,d,J= 5.8 Hz), 7.08 (1H,s), 7.00 (1H,d,J=8.8 Hz), 6.89 (1H,d,J=8.8 Hz), 6.85 (1H,s), 4.43 (2H,t,J=6.2 Hz), 1.8(2H,M), 1.3 (10H,m), 0.9 (3H,t).

SYNTHESIS EXAMPLE 12

3-butoxy-6-hydroxy xanthane

Using the procedure of Synthesis Example 12 and substituting butyl bromide, the title compound was prepared.

SYNTHESIS EXAMPLE 13

3-Octoxy-6-hydroxy xanthane

3-Octoxy-6-hydroxy xanthone (3 mmol) was dissolved in 50 ml of THF. $BH_3$ THF (10 mmol) was added at room temperature and stirred overnight. Dilute HCl (ca. 1N) was added until the bubbling ceased. An additional 3 ml of water was added and the THF was removed. The remaining precipitate was filtered, washed with water and dried yielding 99.3% of 3-octoxy-6-hydroxy xanthane 3(b). $^1$H NMR (DMSO): 9.49 (1H,s), 7.10 (1Hd,J=7.9 Hz), 7.01 (1H,d,J=8.3 Hz), 6.64 (1H,d,J=7.4 Hz), 6.60 (1H,s), 6.49 (1H,d,J=8.5 Hz), 6.43 (1H,s), 3.94 (2H,t,J=6.0 Hz), 3.85 (2H,s), 1.7(2H, m), 1.3 (10H,m), 0.9 (3H,t).

SYNTHESIS EXAMPLE 14

3-Butoxy-6-hydroxy xanthane

Using the procedure of Synthesis Example 13, and substituting 3-butoxy-6-hydroxy xanthane, the title compound was prepared.

SYNTHESIS EXAMPLE 15

5,7-diiodo-3-butyoxy-6-fluorone (DIBF)

3-Butoxy-6-hydroxy xanthane (100 mmol) and $I_2$ (100 mmol) were dissolved in 200 ml of methanol. After $HIO_3$ aqueous solution (100 mmol dissolved in 20 ml of $H_2O$) was dropped slowly into the reaction mixture at 50° C., it was stirred 3 hours. The resulting precipitate was filtered and washed with methanol and dried in a vacuum oven. The yield was 96%.

SYNTHESIS EXAMPLE 16

5,7-diiodo-3-octoxy-6-fluorone (DIOF)

3-Octoxy-6-hydroxy xanthane (2 mmol) and iodine (4 mmol) were dissolved in 30 ml of ethanol. An aqueous solution of iodic acid (4 mmol in 1 ml $H_2O$) was poured into this mixture slowly at room temperature. The reaction mixture was stirred for 1 hour at 60° C., then cooled to 0° C. The resulting orange precipitate was filtered, washed with ethanol to remove iodine, washed with water to remove iodic acid and then washed with ethanol again. The yield of 3,5-diiodo-7-octoxy fluorone (DIOF) was 83.6%. $^1$H NMR ($CDCl_3$): 8.12 (1H,s), 7.72 (1H,s), 7.59 (1H,d,J=8.7 Hz), 7.05 (1H,s), 6.99 (1H,d,J=8.8 Hz), 4.14 (2H,t,J=6.4 Hz), 1.9 (2H,m), 1.4 (10H,m), 0.9 (3H,t).

SYNTHESIS EXAMPLE 17

Synthesis of 9-cyano DIBF

The reaction mixture of DIBF (4 g, 2 mmol) and KCN (6 mmol) in dry DMF (10 ml) was stirred at room temperature. After stirring for 2 hours, the reaction mixture turned deep green. Formic acid (1 ml) was added and the mixture was stirred for 3 more hours. The reaction mixture turned red-purple. Then it was poured into water, extracted with dichloromethane and washed with water. The dichloromethane was removed under reduced pressure to leave the 9-cyano DIBF (DICGF, 5a). DICBF was then purified by using column chromotography. The yield was 54%. $^1$HNMR ($CDCl_3$): 8.48 ppm (1H,s), 7.83 (1H,d,,J=9.5 Hz), 7.05–7.09 (1H,m), 7.04 (1H,s), 4.16 (1H,t,J=6.5 Hz), 1.8–1.9 (1H,m), 1.5–1.6 (4H,m), 1.02 (3H,t,J=7.3 Hz).

3-hydroxy-4,5,7 triiodo-2-octanoyl fluorone and its 9-cyano derivative can be prepared as in Synthesis Examples 18–23.

SYNTHESIS EXAMPLE 18

3,6-dimethoxy xanthone 3,6-Dihydroxy xanthone (1,30 mmol) was dissolved in basic water (NaOH 100 mmol in 200 ml of water). $Me_2SO_4$ was added dropwise and the mixture was stirred for 3 hours at room temperature and 1 hour at 80° C. The resulting precipitate was filtered, washed with NaOH aqueous solution, and then with water yielding 61% of 3,6-dimethoxy xanthone. $^1$HNMR ($CDCl_3$): 8.25 ppm (2H,d,J=8.8 Hz), 6.94 (2H,dd,J1=8.9 Hz,J2=2.4 Hz), 6.87 (2H,d,J=2.2 Hz), 3.94 (6H,s).

SYNTHESIS EXAMPLE 19

3,6-dimethoxy xanthane 3,6-Dimethoxy xanthone (20 mmol) was dissolved in THF. $BH_3$THF was added dropwise at room temperature and the reaction mixture was stirred overnight. HCl (1N) was added until bubbling ceased. 20 ml of water was added and the THF was removed under reduced pressure. The residual solid was filtered, washed with water to give a quantitative amount of 3,6-dimethoxy xanthane. $^1$HNMR ($CDCl_3$): 7.05 ppm (1H,d,J=9.1 Hz), 6.60–6.64 (1H,m), 6.59(1H,s), 3.91(2H,s), 3.80(6H,s).

SYNTHESIS EXAMPLE 20

2-octanoyl-3,6-dimethoxy xanthane 3,6-dimethoxy xanthane (8 mmol) and octanoyl chloride (8 mmol) were dissolved in anhydrous dichlormethane and the solution was cooled with dry ice in ethanol. Aluminum chloride (10 mmol) was added to the solution and the temperature was gradually elevated to room temperature. After stirring for 2 hours at room temperature, the reaction mixture was cooled again with dry ice in ethanol. HCl (1N, 40 ml) was added and the organic compounds were extracted with dichloromethane and washed with water several times. The dichloromethane was removed under reduced pressure. The residual material was almost pure mono-substituted (2 position) compound. The mixture was dissolved in hot hexane and allowed to cool gradually, to give the recrystallized 2-octanoyl-3,6-dimethoxy xanthane in 70% yield. $^1$HNMR ($CDCl_3$): 7.64 ppm(1H,s), 7.09(1H,d,J=8.3 Hz), 6.6–6.7 (1H,M), 6.63 (2H,s), 3.95 (2H,s), 3.92 (3H,s), 3.82 (3H,s), 2.96 (2H,t,J=7.0 Hz), 1.6–1.8 (2H,m), 1.2–1.4 (8H, m)., 0.90 (3H,t).

SYNTHESIS EXAMPLE 21

2-octanoyl-3,6-dihydroxy xanthane

2-Octanoyl-3,6-dimethoxy xanthane (8, 1 mmol) and 5 ml of ethanethiol were dissolved in 20 ml of anhydrous dichloromethane. The mixture was cooled to −15° C. in salt/ice bath. After aluminum chloride (5 mmol) was added, the reaction mixture was heated to room temperature and stirred overnight. The reaction mixture was poured into a mixture of 10 g of ice and 5 ml of conc. HCl to obtain a precipitate. The precipitate was dissolved in NaOH aqueous solution and reprecipitated in dilute HCl. The precipitate was finally filtered, washed with water to yield 50% of 2-octanoyl-3,6-dihydroxy xanthane. $^1$HNMR (DMSO): 12.25 ppm (1H,s), ,9.58 (1H,s), 7.87 (1H,s), 7.06 (1H,d,J=8.3 Hz), 6.58 (2H,s), 6.50 (1H,d,J=8.5 Hz), 3.89 (2H,s), 3.03 (2H,t,J=7.1 Hz), 1.5–1.7 (2H,m), 1.2–1.4 (8H,m), 0.87 (3H,t).

SYNTHESIS EXAMPLE 22

3-hydroxy-4,5,7-triiodo-2-octanoyl-6-fluorone (TIOF)

2-Octanoyl-3,6-dihydroxy xanthane (9, 0.3 mmol) and $I_2$ (0.6 mmol) were dissolved in 3 ml of ethanol. An aqueous solution of $HIO_3$ (0.6 mmol in 0.3 ml of water) was added and the mixture was stirred for 1 hour at room temperature and 3 hours at reflux temperature. The resulting red solid was filtered and washed with ethanol. The yield of 3-hydroxy-2-octanoyl-4,5,7-triiodo-6-fluorone was 67%. The compound showed poor solubility in DMSO and almost no solubility in $CDCl_3$. The NMR in DMSO was hard to analyze.

SYNTHESIS EXAMPLE 23

Synthesis of 9-cyano-3-hydroxy-4,5,7-triiodo-2-octanoyl-6-fluorone

3-Hydroxy-4,5,7-triiodo-2-octanoyl-6-fluorone (10, 0.1 mmol) was dissolved in 3 ml of DMF. KCN (0.3 mmol) was added and the mixture was stirred for 1 hour at room temperature. It was then poured into a dilute solution of HCl to form a purple precipitate. This precipitate was filtered and washed with water giving 9-cyano-3-hydroxy-2-octanoyl-4,5,7-triiodo-6-fluorone in 88% yield. This compound showed very good solubility in $CDCl_3$. $^1$HNMR ($CDCl_3$): 13.93 ppm (1H,s), 8.23 (1H,s), 8.18 (1H,s), 3.15 (2H,t,J=7.3 Hz), 1.7–1.9 (2H,m), 1.2–1.6 (8H,m), 0.94 (3H,t).

The synthesis of 2,7-disubstituted fluorones is shown in Synthesis Examples 24-2.

SYNTHESIS EXAMPLE 24

2,7-Di-t-butyl-3-hydroxy-6-fluorone 8.0 ml of 15–18% fuming sulfuric acid was added dropwise to 3,6-dihydroxyxanthane (10.7 g, 50 mmol.) in 50.0 ml of 2-methyl-2-propanol. The mixture was stirred for 30 minutes and then heated to reflux for one hour. Thereafter 15.0 ml of 2-methyl-2-propanol was added and the solution was refluxed for another 2.5 hours. Upon cooling, the precipitate which formed was filtered and washed with water. 2,7-di-t-butyl-3-hydroxy-6-fluorone (15.8 g) was obtained in 97.5% yield. HNMR(DMSO): 9.11(s,1H), 7.89(s,2H), 7.05(s, 2H), 1.43(s, 18H).

SYNTHESIS EXAMPLE 25

2,7-Di-t-butyl-4,5-diiodo-3-hydroxy-6-fluorone

Iodic acid (352 mg, 2.0 mmol) dissolved in a minimum amount of water was added dropwise to a solution of 1.62 g (5.0 mmol.) of 2,7-di-t-butyl-3-hydroxy-6-fluorone and 1.27 g (10.0 mmol) of iodine in 50 ml of absolute ethanol at 0° C. This mixture was stirred over two hours then 50 ml of cool water was added. The precipitate which formed was filtered and washed with a small amount of ethanol. 2,7-di-t-butyl-yield. HNMR (DMSO): 8.21(s,1H), 7.55(s,2H), 1.38(s,18H).

SYNTHESIS EXAMPLE 26

2,7-Di-t-butyl-4,5-disulfuryl-3-hydroxy-6-fluorone

Fuming sulfuric acid (3.0 ml of 15–18%) was added dropwise to 2,7-di-t-butyl-3-hydroxy-6-fluorone (1.6 g, 4.9 mmol.). The mixture was stirred until the compound dissolved it was slowly warmed to 40°–50° C. for half hour. Ice (10–15 g) was carefully added to the resulting mixture at 0° C. with stirring. The precipitate which formed was filtered and 2,7-di-t-butyl-4,5-disulfuryl-3-hydroxy-6-fluorone (1.72 g) was obtained in 72% yield. HNMR (DMSO): 9.7(s,1H), 8.17(s,2H), 1.40(s,18H).

As the foregoing examples and Reaction Scheme 1 illustrate, the 2- and 7-positions can be functionalized by an electrophilic substitution reaction. Subsequently, the 9-position is functionalized by a 1,6-conjugated addition reaction followed by autooxidation. See for example compounds 8 and 9 in Reaction Scheme 1.

Introduction of functional groups at the 4 and 5 positions may also be accomplished by electrophilic substitution. From 2,7-di-t-butyl-3-hydroxy-6-fluorone, compound 5 in Reaction Scheme 1, 2,7-di-t-butyl-3-hydroxy-4,5-diiodo-6-fluorone can be prepared by reaction with iodine and $HIO_3$. 2,7-Di-t-butyl-3-hydroxy-4,5-disulfuryl-6-fluorone can be prepared from compound 5 by reaction with 15–18% fuming sulfuric acid. Each of these derivatives can be reacted with KCN in DMF using the procedure of Synthesis Example 10 to yield the corresponding 9-cyano derivative.

The 4- and 5-positions can be functionalized as shown in Scheme 2.

Scheme 2

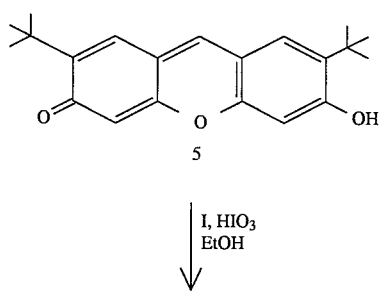

5

I, $HIO_3$
EtOH

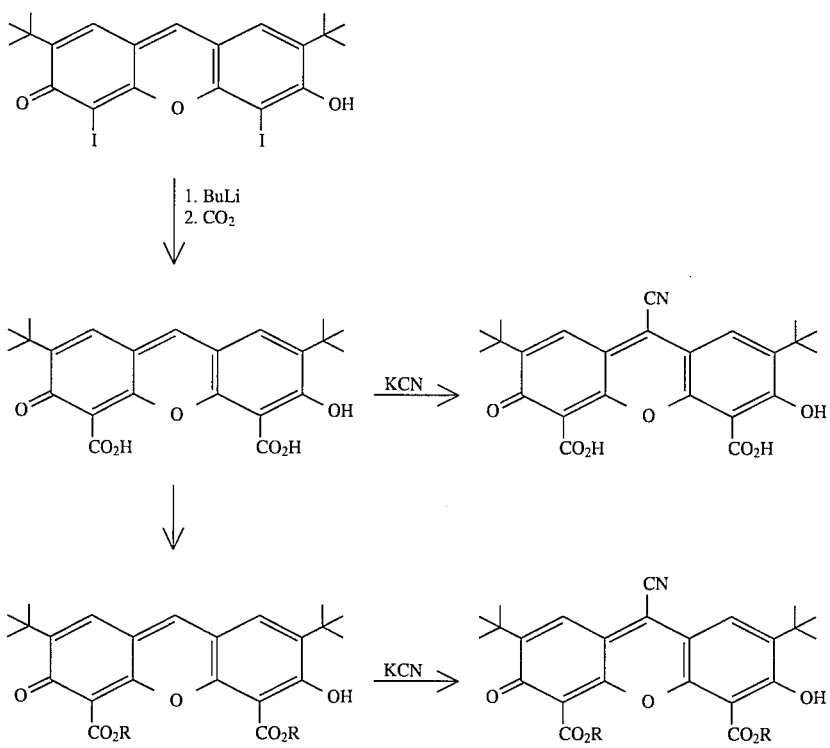

Other 4,5-derivatives can be prepared from 3-hydroxy-4,5-diiodo-6-fluorone (DIHF) which can be prepared as shown in Scheme 3 and illustrated in Synthesis Examples 27 and 28 below:

Scheme 3

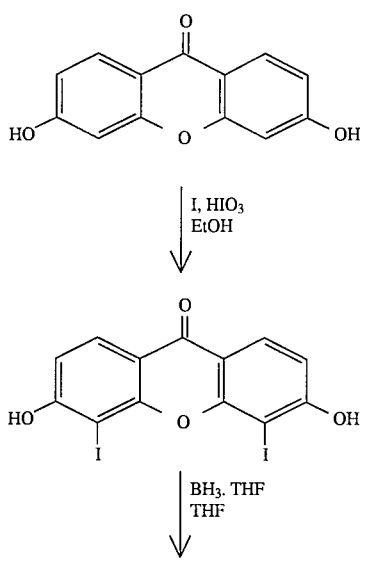

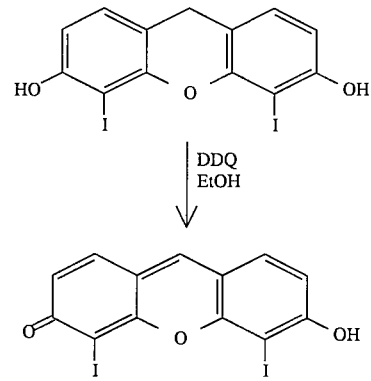

SYNTHESIS EXAMPLE 27

3,6-Dihydroxy-4,5-diiodoxanthane

To a suspension of 3,6-dihydroxy-4,5-diiodoxanthone (9.6 g, 20.0 mmol) in 100 ml of THF was added 40 ml of boran-tetrahydrofuran complex (1.0M in THF) at room temperature under nitrogen. After stirring for 5 hours at room temperature, the reaction mixture was quenched by adding 20.0 ml of 0.5N HCl. After stirring for 30 minutes the solvent was removed. The residue was filtered and the precipitate was dissolved in the 0.1N NaOH solution. This basic solution was filtered and acidified with 0.5N HCl. The yellow solid product which formed was filtered. 3,6-dihydroxy-4,5-diiodoxanthane (9.2 g, 96.6%) was obtained. HNMR (DMSO): 10.38(s,2H), 2.05 (d,2H, J=8.3 Hz), 6.67(d,2H, J=7.8 Hz), 3.88(s,2H).

SYNTHESIS EXAMPLE 28

4,5-Diiodo-3-hydroxy-6-fluorone

To a solution of 3,6-dihydroxy-4,5-diiodoxanthane (233 mg 0.5 mmol) in 10 ml of ethanol at 25° C. was added 2,3-dichloro-5,6-dicyano-1,4-benzoquinone (DDQ) (113 mg, 0.5 mmol). The reaction mixture was stirred for 4 hours at room temperature. The yellow precipitate was filtered and washed with ethanol. 4,5-Diiodo-3-hydroxy-6-fluorone (180 mg) was obtained in 77.6% yield. HNMR (DMSO): 8.22(s, 1H), 7.68(d,2H, J=8.8 Hz), 6.84(d,2H, J=8.3 Hz).

A general procedure for preparation of 9-cyano substituted xanthene derivatives as provided in Example 29.

SYNTHESIS EXAMPLE 29

Potassium cyanide (2.0 mmol) was added to a solution of the corresponding 9-hydrogen substituted xanthene (1.0 in 5.0 ml of DMF. The reaction was monitored by the visible absorption spectrum until the starting material was completely consumed. The reaction solution was treated with 4:1 hexane:dichloromethane after which the precipitate which formed was filtered, dried and treated with 5% HCl and washed with water. 9-Cyano substituted fluorone derivatives were obtained in 80–95% yield. Analytically pure compounds were isolated by TLC separation. The compounds had the properties shown in the table:

| Compound | HNMR (DMSO) |
| --- | --- |
| 9-Cyano-3-hydroxy-6-fluorone | 7.28(d, 2H, J=9.24Hz), 6.28 (dd, 2H, J=9.24, 1.92Hz), 5.94(d, 2H, J=1.98Hz) |
| 9-Cyano-2,4,5,7-tetra-t-butyl-3-hydroxy-6-fluorone | 7.79(s, 2H) |
| 9-Cyano-2,4,5,7-tetraiodo-3-hydroxy-6-fluorone | 8.01(s, 2H) |
| 9-Cyano-4,5-diiodo-3-hydroxy-6-fluorone | 7.38(d, 2H, J=9.2Hz), 6.46 (d, 2H, J=9.2Hz) |
| 9-Cyano-2,7-Di-t-butyl-3-hydroxy-6-fluorone | 7.41(s, 2H), 1.37(s, 18H) |
| 9-Cyano-2,7-di-t-butyl-4,5-diiodo-3-hydroxy-6-fluorone | 7.28(s, 2H), 1.34(s, 18H) |

The synthesis of 2-octyl-4,5,7-triiodo-3-hydroxy-6-fluorone and its 9-cyano derivative is shown in Examples 30–33.

SYNTHESIS EXAMPLE 30

Synthesis of 2-octyl-3,6-dimethoxy xanthane

2-Octanoyl-3,6-dimethoxy xanthane (2 mmol) was dissolved in a mixture of 15 ml of ethanol, 16 ml of ethanol, 16 ml of dichloromethane, 1 ml of water and 0.6 ml of conc. HCl. To this mixture, 0.6 g of activated carbon containing 10 wt % of palladium was added. After stirring overnight under a hydrogen atmosphere, the activated carbon was filtered out and washed with chloroform. The solution was washed with water using a separate funnel. The organic solvents were removed under reduced pressure and the remaining 2-octyl-3,6-dimethoxy xanthane was purified using column chromatography. The yield was 83%. 1H NMR (CDCl$_3$): 7.05 ppm(1H,d,8.8 Hz), 6.88(1H,s), 6.60(1H,dd,8.3 Hz, 2.4 Hz), 6.58(1H,s), 6.54(1H,s), 3.90(2H,s), 3.80(6H,s), 2.54(2H,t,7.2 Hz),1.2–1.4(12H,m),0.9(3H,t) MS m/e for C$_{23}$H$_{30}$O$_3$: Calcd: 354.49: Measured: 354.15

SYNTHESIS EXAMPLE 31

Synthesis of 3,6-Dihydroxy-2-octylxanthane 3,6-dimethoxy-2-octyl xanthane (1.2 mmol), was dissolved in a mixture of 5 ml of ethanethiol and 20 ml of anhydrous dichloromethane. After cooling in a dry ice/EtOH bath, 6 mmol of aluminum chloride was added. The reaction mixture was stirred gradually warming to room temperature overnight. It was then poured into a mixture of 20 g of ice and 10 ml of conc. HCl. The dichloromethane was removed under reduced pressure. The residue was dissolved in aqueous NaOH solution. The solution was then poured into dilute HCl to obtain a precipitate. The precipitate was finally filtered, washed with water to yield in 94%. $^1$H NMR suggested that the compound was a mixture (mp=130°–135° C.) of compounds 3,6-dihydroxy-2-octylxanthane (77%) 6.96 ppm(1H,s), 6.82(1H,s), 6.50–6.52(3H,m), 3.82(2H,s) and an oxidized fluorone form 7.96 ppm (1H,s), 7.53(1H, d,9.3 Hz), 7.41(1H,s), 6.92(2H,s), 6.71(1H,s). Further purification was not attempted because both compounds were thought to yield the same compound the triiodofluorone in the next step. $^1$H NMR in CDCl$_3$/DMSO=10/1 (only for the aromatic ring).

SYNTHESIS EXAMPLE 32

3-hydroxy-4,5,7-triiodo-2-octyl-6-fluorone

The product of Synthesis Example 31 (0.3 mmol) and iodine (0.3 mmol) were dissolved in 3 ml of ethanol. An aqueous solution of iodic acid (0.3 mmol in 0.2 ml of water) was added at room temperature. The reaction mixture was stirred at refluxing temperature for 1 hour. The resulting red precipitate was filtered, washed with ethanol and water mixture to obtain the title compound in 71% yield. $^1$H NMR (DMSO): 8.45 ppm(1H,s), 8.20 (1H,s), 7.61(1H,s), 2.67(2H, t, 7.6 Hz), 1.5–1.6(2H, m), 1.1–1.4(10H,m), 0.85(3H, t, 6.6 Hz).

SYNTHESIS EXAMPLE 33

9-cyano-3-hydroxy-4,5,7-triiodo-2-octyl-6-fluorone

The Product of Example 32 (0.135 mmol) was dissolved in 3 ml of DMF. KCN (0.5 mmol) was added and the reaction mixture was stirred at room temperature. The conversion was monitored with a spectrometer. After 2 hours stirring, the mixture was poured into dilute HCl. The title compound was extracted with chloroform. The chloroform solution was washed with water several times to remove DMF. The chloroform was removed yielding 73% of pure compound. $^1$H NMR (DMSO): 8.14 ppm(1H,s), 7.44(1H,s), 3.14 (2H, t, 7.0 Hz), 0.8–1.6(15H, m). λmax (in EtOH with K$_2$CO$_2$)=630 nm.

The absorption wavelengths of 7-unsubstituted, 7-octanoyl- and 7-octyl-substituted TICHF were 636 nm, 638 nm and 630 nm, respectively. An electron withdrawing acyl group shifted only 2 nm to blue and an electron donating alkyl group shifted 6 nm to red. Substitution on the aromatic ring does not seem to change significantly the maximum absorption wavelength.

Compounds of the general formula (IV) may be obtained by aminomethylation of the corresponding fluorone followed by functionalization of the 9-position or by functionalization of pyronin y using reactions which are analogous to those shown in Reaction Scheme 1 for the fluorones.

Compounds of the formula VI can be prepared by the following Scheme 4:
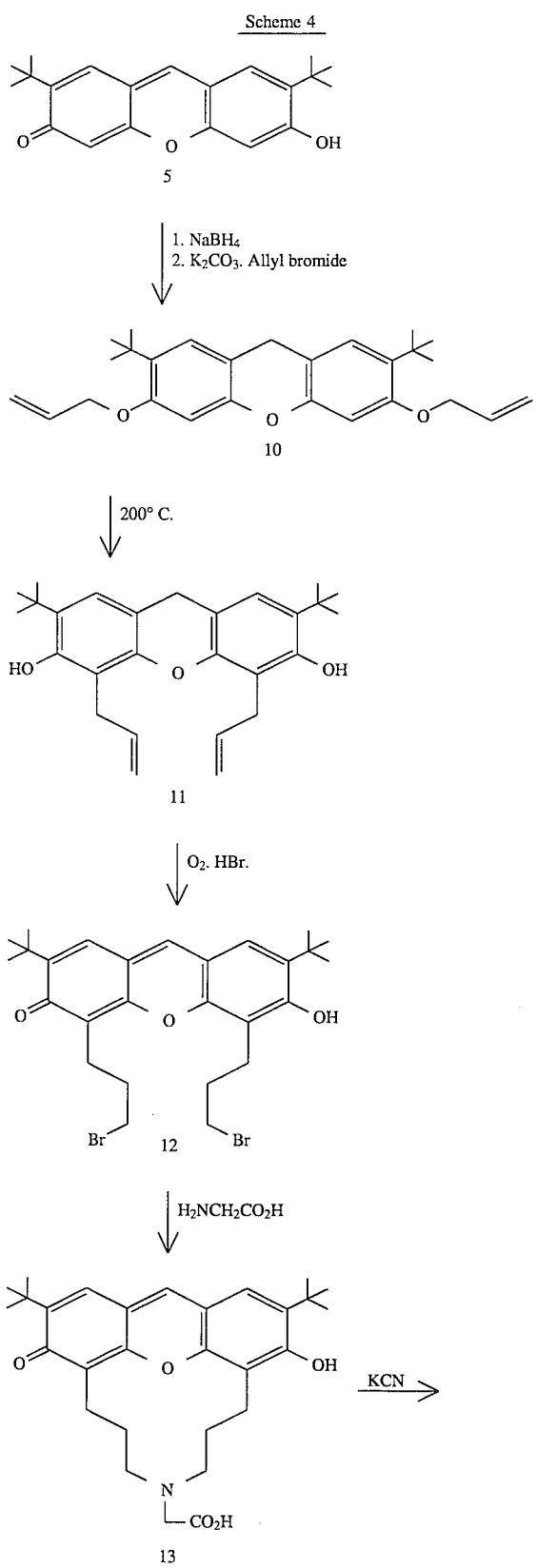
A proposed synthesis for 9-trifluoromethyl derivatives is provided in Scheme 5:
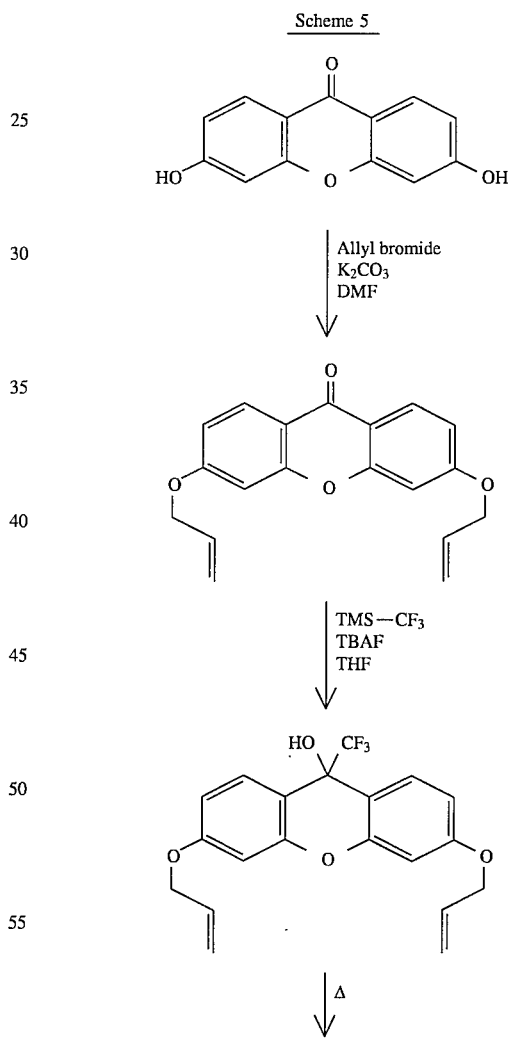

-continued
Scheme 5

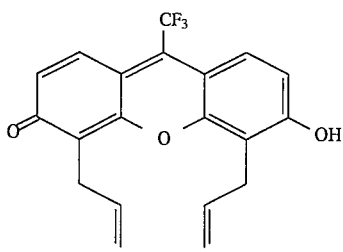

When W is =O and $W^1$ is hydrogen, the compounds are herein referred to as dehydroxyfluorones. A proposed synthetic route for dehydroxyfluorones is shown in Scheme 6 below.

Scheme 6

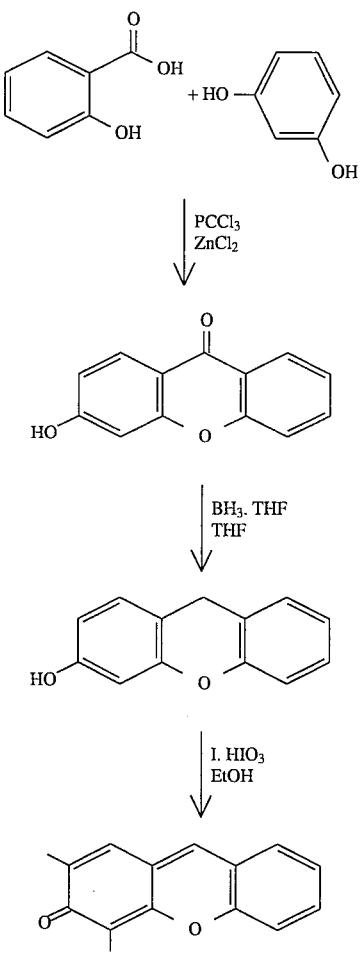

The compounds of the present invention are useful in many of the same applications as conventional photoinitiators and fluorescent dyes. In particular, they are useful as a substitute for fluorescein dyes and other fluorescent agents in immunoassays and still more particularly in polarization immunoassays of the type described in U.S. Pat. No. 4,585,862. The compounds are advantageous because they absorb at much longer wavelengths than conventional fluorescers and this enables the use of inexpensive lasers such as He/Ne lasers to excite the compounds. Furthermore, because of their Long absorption wavelengths, it may be possible to perform immunoassays on whole blood using these compounds. Presently, it is generally necessary to remove the blood cells from the blood in order to prevent them from absorbing the excitation energy.

The compounds of the invention are also useful as fluorescent oil additives for use in engine leak detection. Presently, the fluorescent dyes used in this process require the use of high powered lamps to excite the dye and in order to produce a sufficient level of fluorescence to detect oil leakage due to the competing absorption of the oil and the oil additives. Because the compounds of the invention absorb at longer wavelengths, less competing absorption is encountered and lower power light sources can be used to detect oil leakage. The other components of the oil do not compete as much for the light at longer wavelengths. A particularly preferred fluorescer for use in leak detection is 2,7-di-t-butyl-3-hydroxy-6-fluorone, Compound No. 5 in Reaction Scheme 1 above.

As a result of this photobleachable character, the compositions are also useful in applications in which clear or translucent layer is required as in providing protective coatings for decorative surfaces such as wall and floor panels and in applications in which a high depth of cure is desired.

The fluorone initiators are preferably used in combination with a coinitiator. Coinitiators useful in the present invention can be selected from among those known in the art and, more particularly, from known electron donating coinitiators. N-phenylglycine (NPG) is a well known and preferred coinitiator. Examples of other useful electron donating coinitiators are discussed in Eaton, D. F., "Dye Sensitized Photopolymerization", *Advances in Photochemistry*, Vol. 13, pp. 427–486. N,N-dialkylanilines are also particularly useful. Other tertiary amines such as diethanolamine, triethanolamine, and arylsulfinates can also be used.

Dialkylanilines appear to function as autoxidizers and are preferably used in combination with an electron donor such as NPG. Representative examples of N,N-dialkylanilines useful in the present invention are diisopropyldimethylaniline (DIDMA), 4-cyano-N,N-dimethylaniline, 4-acetyl-N,N-dimethylaniline, 4-bromo-N,N-dimethylaniline, 4-methyl-N,N-dimethylaniline, 4-ethoxy-N,N-dimethylaniline, N,N-dimethylthioaniciidine, 4-amino-N,N-dimethylaniline, 3-hydroxy-N,N-dimethylaniline, N,N,N'N'-tetramethyl-1,4-dianiline, 4-acetamido-N,N-dimethylaniline, 2,6-diethyl-N,N-dimethylaniline, N,N,2,4,6-pentamethylaniline (PMA) and p-t-butyl-N,N-dimethylaniline.

Another class of useful coinitiators is alkyl borate salts such as ammonium and pyridinium salts of tetrahydrocarbyl boranyl anions. Useful boranylanions are disclosed in U.S. Pat. No. 4,772,541.

The most typical example of a free radical addition polymerizable or crosslinkable compound useful in the present invention is an ethylenically unsaturated compound and, more specifically, a polyethylenically unsaturated compound. These compounds include both monomers having one or more ethylenically unsaturated groups, such as vinyl or allyl groups, and polymers having terminal or pendant ethylenic unsaturation. Generally, any unsaturated compound which is convertible to a solid by free radical polymerization is useful herein. Such compounds are well known in the art and include acrylic and methacrylic esters of polyhydric alcohols such as trimethylolpropane, pentaerythritol, and the like; and acrylate or methacrylate terminated epoxy resins, acrylate or methacrylate terminated polyesters, etc. Representative examples include ethylene glycol diacrylate, ethylene glycol dimethacrylate, trimethylolpropane triacrylate (TMPTA), pentaerythritol tetramethacrylate, dipentaerythritol hydroxypentacrylate (DPHPA), hexanediol-1,6-dimethacrylate, hexanediol diacrylate, diethyleneglycol dimethacrylate, diglycidyl ether diacrylate (MW=390), trimethylol propane ethoxylate triacrylate, neopentyl glycol propoxylate diacrylate, tripropylene glycol diacrylate (MW=300)(TPGDA). Other vinyl compounds such as N-vinyl pyrrolidone (NVP) are also useful. The monomers may be selected and blended to provide the optimum photographic speed and/or the physical characteristics desired in the product. Monomer selection and blending may also be used to insure adequate solubility of the photoinitiators.

It may be desirable to incorporate a sensitizer in the compositions of the present invention to control the sensitivity of the composition and/or to extend its sensitivity. Useful sensitizers include those known in the art such as anthracene, and its derivatives naphthalene, acetophenone, benzophenone, 2-acetonaphthone, etc.

Solvents may be necessary to dissolve the photoinitiator if the photoinitiator is not sufficiently soluble in the monomer. Solvents may also be used to shift the absorption spectrum to tune the sensitivity of the composition. Some examples of useful solvents are N-vinylpyrrolidone and nitrobenzene. Other useful solvents can be identified readily.

The nature of the monomer, the amount of the fluorone and coinitiator in photohardenable compositions in accordance with the present invention will vary with the particular use of the compositions, the emission characteristics of the exposure sources, the development procedures, the physical properties desired in the polymerized product and other factors. With this understanding, compositions in accordance with the invention will generally fall within the following compositional ranges in parts by weight (based on 100 parts total):

| | |
|---|---|
| Polymerizable compound | 50 to 99.7 |
| Fluorone | 0.01 to 0.20 |
| Electron Donor | 0.2 to 4 |
| Autoxidizer | 0 to 3 |
| Sensitizer (optional) | 0.3 to 1. |

Compositions in accordance with the invention more typically are anticipated to have the following formulation:

| | |
|---|---|
| Polymerizable compound | 10 |
| Fluorone | .002 to .010 |
| Electron Donor | .02 to .1 |
| Autoxidizer | 0 to 3 g |
| Sensitizer (optional) | .02 to .1 |

Examples of some photosensitive compositions incorporating photoinitiators in accordance with the invention are provided in Example 35.

EXAMPLE 34

The following compositions were prepared:

| | |
|---|---|
| Composition 1 | |
| TMPTA | 90 g |
| NVP | 10 g |
| TIHF | 3.6 mg |
| NPG | 75 mg |
| Composition 2 | |
| DPHPA | 87 g |
| NVP | 13 g |
| NPG | 3.6 mg |
| TIHF | 75 mg |
| Composition 3 | |
| DPHPA | 30 g |
| NVP | 10 g |
| TIHF | 3.6 mg |
| NPG | 75 mg |
| TMPTA | 20 g |
| Ebecryl 3700 (bisphenol A diacrylate) | 4 oz. |
| Composition 4 | |
| NVP | 10 g |
| TIHF | 3.6 mg |
| NPG | 75 mg |
| Tetraethylene glycol diacrylate | 90 g |

RESULTS

Each composition was placed in a test tube and exposed to a broad band light source. The compositions all cured rapidly.

In addition to being useful in photosensitive materials, the compositions of the present invention are also useful in a wide variety of other applications including photocurable inks and coatings, photoadhesives, printing plates, printed circuit fabrication, and other applications for photohardenable compositions.

One of the advantages of the fluorone dye photoinitiators in this invention is the depth of the cure that is obtainable. This is in contrast to UV photoinitiators that causes a "screening" effect which prevents the UV light from penetrating beyond a certain minimum depth, usually several millimeters. By contrast, the fluorone dye bleaches as it photoinitiates and is concommitantly converted into a non-visible absorbing species thus allowing more visible light to penetrate which continues the cure. This cascading bleaching effect permits substantial depth of cure which can easily reach several inches.

An acrylate monomer mixture was composed of 15 parts urethane diacrylate, 20 parts TPGPA, 40 parts TMPTA and 15 parts DPHPA, and a 20 to 1 weight ratio of NPG coinitiator to DIEF or DIBF fluorone dye. For dye concentrations of 0.01, 0.05 and 0.1 weight, all the formulations cured to a depth of 3 cm in 30 seconds when exposed to a 350 watt tungsten halogen light which provides about 500 mw/cm$^2$ irradiance. When the irradiance was increased to about 2 watts/cm$^2$ cure speed was shortened to 5 seconds for the same depth.

An acrylate mixture was composed of 60% urethane diacrylate, 30% DPHPA, 10% BDDA, and 0.05 weight % of DIEF or DIBF fluorone dye with 2 weight % of DIDMA. The formulation cure to a depth greater than 1 cm in 10 seconds when exposed to a 75 watt tungsten halogen lamp which provided an irradiance of about 260 mw/cm$^2$.

An acrylate mixture was composed of 33% TMPTA, 33% DPHPA, 33% Epoxy acrylate, and 2% of DIDMA with either 0.01, 0.05 or 0.1 weight % of DIEF. All samples cured to a depth greater than 1 cm in 10 seconds when exposed to a 75 watt tungsten halogen.

An acrylate mixture was composed of 70% urethane diacrylate, 5% DPHPA, 25% BDDA, and 2% DIDMA with either 0.01, 0.03 or 0.1 weight % DIEF. The 0.01 and 0.03 samples cured after 2 passes through a 300 watt per inch medium pressure mercury arc lamp at a speed of 50 feet/ minute to a depth greater than 3 mm. The 0.1 sample cured to a depth of greater than 1.5 mm.

The depth of cure results have also been observed with other fluorone dyes as part of this invention that absorb throughout the visible spectrum inlcuding TIHF and TIHCF.

While the invention has thus far been described with regard to free radical polymerizable compositions, the fluorones described herein are also useful in ionically polymerizable compositions and more particularly cationically polymerizable compositions. The fluorones may be used in combination with onium salts such as iodonium, phosphonium, sulfonium and pyrylium salts. Compositions containing onium salts are capable of generating free radicals as well as cations and may be used to provide photohardenable compositions which react by either or both mechanisms. The fluorone may react as an electron donor or as an electron acceptor depending upon the nature of the coinitiator and onium salt (if present). In free radical polymerizable composition such as those illustrated in Example 34, the fluorone is an electron acceptor whereas in compositions such as those illustrated in Examples 35–37 below and in cationic polymerization the fluorone is believed to react as an electron donor.

Cationically polymerizable compositions based upon onium salts are known in the art as shown in U.S. Pat. Nos. 4,264,703 and 4,307,177 to Crivello, and European Application 0 408 227 A1.

Examples of onium salts useful in the invention can be found in published European Patent Application 0 408227A1. The preferred onium salts for use in the invention are diphenyliodonium salts such as diphenyliodonium hexafluorophosphate, arsenates, antimonates, etc., and, more particularly, hexafluoro-antimonate. Onium salts of simple anions such as chlorides, bromides, etc. are also useful in free radical polymerizable compositions. A particularly preferred onium salt is OPPI below. Addition of a coinitiator such as NPG improves film speed, pencil hardness and double bond conversion. A particularly preferred initiator system is a combination of an iodofluorone in accordance with the invention such as TIHF or DIBF, an amine such as NPG or DIDMA and an onium salt. A preferred molar ratio of fluorone to onium salt to amine is about 1:2:3. Keeping this ratio constant, the double bond conversion has been observed to increase as the molar concentration of the fluorone increases from 0.001 to 0.003 molar. These onium salt formulations are illustrated in the following Examples 35–37.

In accordance with one embodiment of the invention the fluorone may be metathesized with an onium salt to form an ionically bonded complex of one or two onium cations and the fluorone dye anion. Complex formation occurs at the 6-position when W=O as well as at the 3-position when $W^1$ is $O^-$ in formula (III).

EXAMPLE 35

To a resin formulation consisting of 15 parts urethane diacrylate, 15 parts DPHPA, 20 parts TPGDA and 40 parts TMPTA was added DIDMA, initiator and (4-octyloxyphenyl)phenyliodonium hexafluoroantimonate (OPPI). The samples were coated to a thickness of 15 microns and exposed to a 75 W tungsten halogen dental lamp (focused through an optical fiber) at a distance of 0.75 inch at which the Light intensity was about 0.40 W/cm². The molar ratios are indicative of the amounts of fluorone to onium salt to amine coinitiator. The double bond conversion was determined by FTIR spectroscopy. The pencil hardness of a given test sample is measured by holding a pencil at a 45° angle to the sample and drawing across it towards the person testing it. Using the pencils in an order from softest to hardest, the first pencil that scratches the surface is assigned as the pencil hardness of the sample. The pencil hardness scale is as follows from softest to hardest: 4B, 3B, 2B, B, HB, H, 2H, 3H, 4H, 6H. For instance, if a 2H pencil is the first pencil to scratch the surface then the pencil hardness is 2H.

At the extreme ends of the scale, it is impossible to determine the actual pencil hardness. If the 6H pencil does not scratch the sample, the only assignment that can be made is that it is >6H. Likewise, if the 4B pencil scratches the sample, the only assignment that can be made is <4B, unless it is a lot softer than 4B in which case a <<4B can be assigned. A pencil hardness of 4H is generally considered satisfactory. Pencil hardness data was greater than 6H after 30 seocnd exposure for all samples except for the control samples without amine (1:2:0). The controls were all less than 4B an 0.05 wt %, 0.10 wt %, and 0.15 wt %. The results are shown in Table 4.

TABLE 4

| Initiator | CONC. | Molar Ratio | Coinitiator | Exp. Time | C=C% Conversion |
|---|---|---|---|---|---|
| DIBF | 0.05 wt % | (1:2:0) | DIDMA | 30 sec | 5% |
| DIBF | 0.10 wt % | (1:2:0) | DIDMA | 30 sec | 18% |
| DIBF | 0.15 wt % | (1:2:0) | DIDMA | 30 sec | 19% |
| DIBF | 0.05 wt % | (1:0:60) | DIDMA | 30 sec | 37% |
| DIBF | 0.05 wt % | (1:1:60) | DIDMA | 30 sec | 37% |
| DIBF | 0.05 wt % | (1:2:3) | DIDMA | 30 sec | 40% |
| DIBF | 0.05 wt % | (1:2:5) | DIDMA | 30 sec | 40% |
| DIBF | 0.05 wt % | (1:2:60) | DIDMA | 30 sec | 43% |
| DIBF | 0.05 wt % | (1:2:3) | NPG | 30 sec | 40% |
| DIBF | 0.05 wt % | (1:2:3) | DIDMA | 30 sec | 40% |
| DIBF | 0.10 wt % | (1:2:3) | DIDMA | 30 sec | 45% |
| DIBF | 0.15 wt % | (1:2:3) | DIDMA | 30 sec | 50% |
| DIBF | 0.20 wt % | (1:2:3) | DIDMA | 30 sec | 51% |
| DIBF | 0.25 wt % | (1:2:3) | DIDMA | 30 sec | 50% |
| DIBF | 0.05 wt % | (1:2:3) | NPG | 60 sec | 43% |
| DIBF | 0.05 wt % | (1:2:3) | DIDMA | 60 sec | 43% |
| DIBF | 0.10 wt % | (1:2:3) | DIDMA | 60 sec | 47% |
| DIBF | 0.15 wt % | (1:2:3) | DIDMA | 60 sec | 54% |
| DIEF | 0.05 wt % | (1:2:3) | DIDMA | 30 sec | 40% |
| DIOF | 0.15 wt % | (1:2:3) | DIDMA | 30 sec | 40% |
| DIOF | 0.05 wt % | (1:2:3) | DIDMA | 30 sec | 40% |

The foregoing study was repeated using 100% butanediol diacrylate, and 100% polyethylene glycol diacrylate (MW=400)(PEGA 400). The results are shown in Table 5 that follows:

TABLE 5

| Initiator | CONC. | Molar Ratio | Coinitiator | Exp. Time | C=C% Conversion |
|---|---|---|---|---|---|
| 100% Butane Diol Diacrylate (BDDA): | | | | | |
| DIBF | 0.05 wt % | (1:0:60) | DIDMA | 30 sec | 30% |
| DIBF | 0.05 wt % | (1:2:3) | DIDMA | 30 sec | 49% |
| DIBF | 0.10 wt % | (1:2:3) | DIDMA | 30 sec | 56% |
| DIBF | 0.10 wt % | (1:2:3) | DIDMA | 60 sec | 56% |
| DIBF | 0.15 wt % | (1:3:3) | DIDMA | 30 sec | 58% |
| 100% Polyethylene Glycol Diacrylate (PEGA400) | | | | | |
| DIBF | 0.05 wt % | (1:0:60) | DIDMA | 60 sec | 50% |
| DIBF | 0.05 wt % | (1:2:3) | DIDMA | 60 sec | 61% |
| DIBF | 0.10 wt % | (1:2:3) | DIDMA | 60 sec | 90% |

TABLE 5-continued

| Initiator | CONC. | Molar Ratio | Coinitiator | Exp. Time | C=C% Conversion |
|---|---|---|---|---|---|
| DIBF | 0.15 wt % | (1:2:3) | DIDMA | 60 sec | 90% |
| DIBF | 0.15 wt % | (1:2:3) | DIDMA | 30 sec | 84% |
| DIBF | 0.15 wt % | (1:2:3) | DIDMA | 10 sec | 60% |

EXAMPLE 36

Photosensitive compositions were prepared from the resin formulation of Example 35 containing 1% NPG and 0.05% DIBF or 0.05% DIEF. The samples were exposed under the conditions shown in the following table and pencil hardness was measured. The results are shown in Table 6.

TABLE 6

| Light Source | Conditions | Time | 0.05 wt. % DIBF | 0.05 wt. % DIEF |
|---|---|---|---|---|
| Dental Lamp | No Air | 60 sec | >6H | 3H |
| Dental Lamp | No Air | 30 sec | >6H | 2H |
| Dental Lamp | No Air | 10 sec | 4H | <4B |
| Dental Lamp | Air | 60 sec | H | 2B |
| Fusion (Q bulb) | Air | 10 ft/min | >6H | >6H |
| Fusion (Q bulb) | Air | 20 ft/min | 4H | 3H |
| Overhead Proj. | No Air | 60 sec | 5–6H | 3H |
| Overhead Proj. | Air | 60 sec | H | 3B |

Diphenyliodonium hexafluoroantimonate was added to DIBF samples. The results are shown in Table 7.

TABLE 7

| Light Source | Conditions | Time | 0.05 wt. % DIBF (w/ 0.05 wt. % DPISbF6) |
|---|---|---|---|
| Dental Lamp | No Air | 10 sec | >6H |
| Dental Lamp | Air | 60 sec | 2H |
| Fusion (Q bulb) | Air | 10 ft/min | >6H |
| Fusion (Q bulb) | Air | 20 ft/min | >6H |

Samples were also prepared using 1% DIDMA in addition to the fluorone for a 20:1 weight ratio. The exposure conditions and pencil hardness are shown in the following Table 8.

TABLE 8

| Light Source | Conditions | Time | 0.05 wt. % DIBF | 0.05 wt. % DIEF |
|---|---|---|---|---|
| Dental Lamp | No Air | 60 sec | >6H | 2B |
| Dental Lamp | No Air | 30 sec | >6H | 3B |
| Dental Lamp | No Air | 10 sec | 5–6H | (not tested) |
| Dental Lamp | Air | 60 sec | H | 3B |
| Fusion (Q bulb) | Air | 10 ft/min | >6H | 2B |
| Fusion (Q bulb) | Air | 20 ft/min | 3H | >4B |

Samples were also prepared from the same resin formulation containing 0.1% DIBF in addition to the coinitiator listed in the following Table 9 with the exposure condition and pencil hardness results shown.

TABLE 9

| Light Source | Conditions | Time | 1.5% DIDMA | 1.5% NPG | 2% NPG |
|---|---|---|---|---|---|
| Dental Lamp | No Air | 60 sec | >6h | >6H | >6H |
| Dental Lamp | No Air | 30 sec | >6H | >6H | >6H |
| Dental Lamp | No Air | 10 sec | >6H | 5–6H | 5–6H |
| Dental Lamp | Air | 60 sec | H | H | H |
| Fusion (Q bulb) | Air | 10 ft/min | >6H | >6H | >6H |
| Fusion (Q bulb) | Air | 20 ft/min | 5–6H | 5–6H | 5–6H |

EXAMPLE 37

Using the resin formulation of Example 36, photosensitive compositions were prepared using TIHF, DIDMA and OPPI at a concentration of 0.21% and in the molar ratios shown in Table 10 which follows. Exposure was conducted with the dental lamp at a distance of 1 inch from the sample to provide an intensity of about 0.26 W/cm$^2$. Molar ratios are fluorone:onium salt:amine.

TABLE 10

| Molar Ratio | Exp. Time | Pencil Hardness |
|---|---|---|
| (1:1:0) | 60 sec. | 4H |
| (1:2:0) | 60 sec. | 5–6H |
| (1:5:) | 60 sec. | 5–6H |
| (1:10:0) | 60 sec. | 5–6H |
| (1:1:0) | 60 sec. | 4H |
| (1:1:1) | 60 sec. | 5–6H |
| (1:1:5) | 60 sec. | >6H |
| (1:1:10) | 60 sec. | >6H |
| (1:1:33) | 60 sec. | >6H |
| (1:2:0) | 60 sec. | 5–6H |
| (1:2:10) | 60 sec. | >6H |
| (1:2:5) | 60 sec. | >6H |
| (1:2:10) | 60 sec. | >6H |
| (1:2:33) | 60 sec. | >6H |

EXAMPLE 38

Example 37 was repeated using DIBF in place of TIHF in the concentration and molar ratios shown in the following Table 11.

TABLE 11

| Conc. | Molar Ratio | Conitiator | Exp. Time | Pencil Hardness |
|---|---|---|---|---|
| 0.05% | (1:2:3) | NPG | 60 sec. | >6H |
| 0.05% | (1:2:3) | DIDMA | 60 sec. | >6H |
| 0.10% | (1:2:3) | DIDMA | 60 sec. | >6H |
| 0.15% | (1:2:3) | DIDMA | 60 sec. | >6H |
| 0.05% | (1:0:60) | DIDMA | 60 sec. | >6H |
| 0.05% | (1:0:60) | DIDMA | 60 sec. | >6H |
| 0.05% | (1:0:60) | DIDMA | 10 sec. | 4H |
| 0.05% | (1:1:60) | DIDMA | 10 sec. | >6H |

EXAMPLE 39

This example illustrates the preparation of an onium salt complex from TIHF and diphenyliodonium chloride.

7.15 g TIHF was washed with diluted HCl solution and subsequently washed with a large quantity of $H_2O$ to make sure all the dye is in the acidic form. The TIHF was dissolved in 65 Ml DMF. Fresh $Ag_2O$ was prepared by mixing approximately equimolar aqueous solutions of $AgNO_3$ and NaOH together, the precipitated black $Ag_2O$ was filtered and washed with large quantity of distilled water. 2.2 g moist $Ag_2O$ and 3.5 g diphenyliodonium chloride were mixed together in a glass mortar. The reagents were thoroughly ground together until no trace of iodonium compound could be discerned. The black slurry was then washed into a sintered glass filter and the precipitate washed with H$_2$O until 35 ml filtrate was obtained. The filtrate was filtered again until the solution of diphenyliodonium hydroxide was transparent. The DMF solution of TIHF and the aqueous solution of diphenyliodonium hydroxide was mixed together and the DMF/H$_2$O solvent was vacuum distilled off until only a small volume remained. The dye onium complex salt was precipitated from the solution by adding a large quantity of H$_2$O, and dried in an oven at 60° C. overnight. The yield is 80%.

The photohardenable compositions of the present invention can be coated upon a support in a conventional manner and used in making a photoresist or in photolithography to form an oleophilic polymer image. Development of photohardenable compositions in accordance with the invention is conducted in an otherwise known or conventional manner, e.g., a solvent for the unpolymerized monomer may be used to remove the photohardenable composition in the unexposed areas.

The compositions of the invention can also be encapsulated as described in U.S. Pat. Nos. 4,399,209 and 4,440,846 and used to control the release of an image-forming agent. The latter processes typically involve image-wise exposing the photosensitive layer to actinic radiation and subjecting the layer of microcapsules to a uniform rupturing force such as pressure.

The photohardenable composition of the invention are also advantageous for use in the three dimensional modeling process taught in U.S. Pat. No. 4,575,330 to Hull. Due to the thicker depth of cure that is possible, models may be prepared in larger cross-sectional increments. This should reduce the total time required for the model building process. Another advantage which the claimed compounds bring to three dimensional modeling is higher green strength.

Generally, fluorones in accordance with the invention absorb at about 360 to 635 nm. It is anticipated that sensitivity can be extended to longer wavelengths by substituting electron donating groups for R. Depending upon the extinction coefficient, compositions and photosensitive materials in accordance with the invention can be exposed to any source which emits in this range and particularly an He/Cd laser, or mercury arc lamps.

The invention also includes the use of fluorones in dosimeters and more particularly in dosimeters useful in wave length sensitive laser dosimeters.

Having described the invention in detail and by reference to preferred embodiments thereof, it will be apparent that modifications and variations are possible without departing from the scope of the invention defined in the appended claims.

What is claimed is:

1. A compound of the formula (I) or (II):

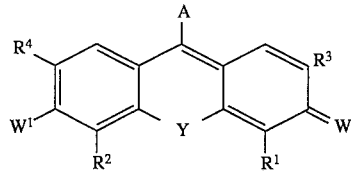

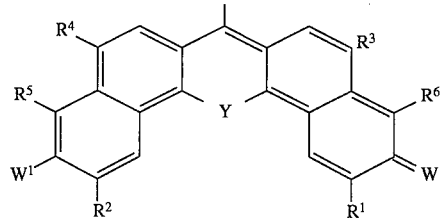

where $R^1$, $R^2$, $R^3$ and $R^6$ are the same or different and represent a hydrogen atom or a halogen atom and $R^1$ and $R^2$ may combine to form a ring; $R^3$, and $R^4$ are the same or different and represent a hydrogen atom, a halogen atom, a benzoyl group, a group of the formula —L(CH$_2$)$_n$R$^8$ where n is 1 to 8, R$^8$ is a hydrogen, hydroxy, amino, dialkylamino, —COR$^{16}$ or —COOR$^{14}$ where R$^{16}$ is a hydrogen, chlorine, COCl, C$_1$–C$_8$ alkyl, —NR$_2$ or aryl and R$^{14}$ is a hydrogen, C$_1$–C$_8$ alkyl, aryl, COR, 2,4-dinitrophenyl, N-imido or —NR$_2$ and L is a direct bond or C=O; W is =O; W$^1$ is hydrogen or —OR$^9$, where R$^9$ is hydrogen, C$_1$–C$_8$ alkyl, acyl or a group of the formula —(CH$_2$)$_n$R$^{10}$ where n is 1 to 8 and R$^{10}$ is amino, dialkylamino, hydroxy, acryloyl or methacryloyl; Y is oxygen, sulfur, selenium, tellurium, C=O, or >N—R$^{13}$ is where R$^{13}$ is 4-methylphenyl, and A is hydrogen, alkenyl, dichlorotriazinylamino, or an electron withdrawing group selected from the group consisting of COOR$^{11}$, C(O)OCOR$^{11}$, CONR$_2$, CN, NO$_2$, NCS, NCO, SO$_2$R$^{12}$, SO$_3$, R$^{12}$, SO$_3$R$^{11}$, SO$_2$NR$_2$ and CX$_3^2$ where X$^2$ is the same or different and is a halogen atom and R$^{11}$ is hydrogen, alkyl, aryl, or aralkyl, and R$^{12}$ is hydrogen, alkyl, aryl, or aralkyl; provided that when R$^1$–R$^6$ are all hydrogen, A is not hydrogen.

2. The compound of claim 1 wherein said compound is represented by the Formula (I).

3. The compound of claim 1 wherein Y is O.

4. The compound of claim 1 wherein at least two of R$^1$–R$^4$ are iodo or bromo.

5. The compound of claim 1 wherein none of R$^1$–R$^4$ is halogen and R$^9$ is hydrogen.

6. The compound of claim 4 wherein A is hydrogen.

7. The compound of claim 1 wherein A is CN.

8. The compound of claim 5 wherein A is CN.

9. The compound of claim 5 wherein A is hydrogen.

10. The compound of claim 1 wherein A is CF$_3$.

11. The compound of claim 5 wherein said compound includes a functional group suitable for coupling said compound to a ligand-analog or an antibody.

12. The compound of claim 11 wherein said compound in represented by the formula

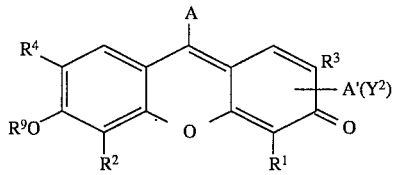

where A' is a ligand analog or an antibody, and Y$^2$ is a linking group.

13. The compound of claim 2 wherein Y is oxygen, sulfur or >NR$^{13}$ where R$^{13}$ is 4-methylphenyl; and W is =O.

14. The compound of claim 13 wherein R$^1$ and R$^2$ combine to form a ring.

15. The compound of claim 5 wherein at least one of R$^1$–R$^4$ includes a functional group which produces intramolecular ionization of said compound.

16. The compound of claim 4 wherein at least two of $R^1$–$R^4$ are iodo.

17. The compound of claim 4 wherein $W^1$ is $OR^9$ and $R^9$ is $C_1$–$C_8$ alkyl.

18. The compound of claim 4 wherein said compound is selected from the group consisting of:
  5,7-diiodo-3-methoxy-6-fluorone (DIMF),
  5,7-diiodo-3-ethoxy-6-fluorone (DIEF),
  5,7-diiodo-3-butoxy-6-fluorone (DIBF),
  5,7-diiodo-3-octoxy-6-fluorone (DIOF),
  4,5-diiodo-3-hydroxy-6-fluorone,
  9-cyano-5,7-diiodo-3-methoxy-6-fluorone (CDIMF),
  9-cyano-5,7-diiodo-3-ethoxy-6-fluorone (CDIEF),
  9-cyano-5,7-diiodo-3-butoxy-6-fluoorone (CDIBF),
  9-cyano-5,7-diiodo-3-octoxy-6-fluorone (CDIOF),
  3-hydroxy-2,4,5,7-tetraiodo-6-fluorone (TIHF),
  3-hydroxy-2,4,5,7-tetrabromo-6-fluorone (TBHF),
  3-hydroxy-2,4,5,7-tetrachloro-6-fluorone (TCHF),
  3-hydroxy-2,4,5,7-tetrafluoro-6-fluorone (TFHF),
  9-cyano-3-hydroxy-2,4,5,7-tetraiodo-6-fluorone (TIHCF),
  9-cyano-3-hydroxy-2,4,5,7-tetrabromo-6-fluorone (TBHCF),
  9-cyano-3-hydroxy-2,4,5,7-tetrachloro-6-fluorone (TCHCF),
  9-cyano-3-hydroxy-2,4,5,7-tetrafluoro-6-fluorone (TFHCF),
  3-hydroxy-4,5,7-triiodo-2octanoyl-6-fluorone,
  9-cyano-3-hydroxy-4,5,7-triiodo-2-octanoyl-6-fluorone,
  3-hydroxy-4,5,7-triiodo-2-octanoyl-6-fluorone,
  9-cyano-3-hydroxy-4,5,7-triiodo-2-octyl-6-fluorone,
  3-hydroxy-2,4,5,7-tetraiodo-6-thiafluorone,
  3-hydroxy-4,5,7-triiodo-2-pentanoyl-6-fluorone,
  9-cyano-3-hydroxy-4,5,7-triiodo-2-pentanoyl-6-fluorone,
  3-hydroxy-4,5,7-triiodo-2-pentyl-6-fluorone,
  9-cyano-3-hydroxy-4,5,7-triiodo-2-pentyl-6-fluorone,
  2,7-di-t-butyl-4,5-diiodo-3-hydroxy-6-fluorone,
  9-cyano-2,7-di-t-butyl-4,5-diiodo-3-hydroxy-6-fluorone, and
  7-benzoyl-2,4,5-triiodo-3-hydroxy-6-fluorone.

19. The compound of claim 5 wherein said compound is selected from the group consisting of:
  3-hydroxy-6-thiafluorone,
  2,7-di-t-butyl-3-hydroxy-6-fluorone,
  9-cyano-2,7-di-t-butyl-3-hydroxy-6-fluorone,
  2,7-di-t-butyl-4,5-carboxymethyl-3-hydroxy-6-fluorone,
  9-cyano-2,7-di-t-butyl-4,5-carboxymethyl-3-hydroxy-6-fluorone,
  9-trifluoromethyl-2,7-di-t-butyl-3-hydroxy-6-fluorone,
  9-trifluoromethyl-2,7-di-t-butyl-4,5-carboxymethyl-3-hydroxy-6-fluorone,
  9-trifluoromethyl-3-hydroxy-6-fluorone,
  3-hydroxy-7-pentanoic acid-6-fluorone,
  3-hydroxy-7-butyric acid-6-fluorone,
  9-cyano-3-hydroxy-7-pentanoic acid-6-fluorone,
  2,7-dicitronellicacid-3-hydroxy-6-fluorone, and
  9-cyano-2,7-dicitronellicacid-3-hydroxy-6-fluorone.

20. The compound of claim 4 wherein $R^{10}$ is acryloyl or methacryloyl.

* * * * *

UNITED STATES PATENT AND TRADEMARK OFFICE
CERTIFICATE OF CORRECTION

PATENT NO. : 5,623,080
DATED : April 22, 1997
INVENTOR(S) : Douglas C. Neckers et al.

It is certified that error appears in the above-indentified patent and that said Letters Patent is hereby corrected as shown below:

Col. 30, line 11 (claim 1), "$R^3$" should be --$R^5$--.

Col. 30, line 48 (claim 12), "in" should be --is--.

Signed and Sealed this

Seventeenth Day of June, 1997

Attest:

BRUCE LEHMAN

Attesting Officer

Commissioner of Patents and Trademarks